United States Patent
Carothers

(10) Patent No.: US 11,747,283 B2
(45) Date of Patent: Sep. 5, 2023

(54) DOCKING STATION WITH WAVEGUIDE ENHANCED ANALYTE DETECTION STRIP

(71) Applicant: STRIKE PHTONICS, INC, Dallas, TX (US)

(72) Inventor: Daniel Carothers, Lucas, TX (US)

(73) Assignee: Strike Photonics, Inc., Allen, TX (US)

( * ) Notice: Subject to any disclaimer, the term of this patent is extended or adjusted under 35 U.S.C. 154(b) by 190 days.

(21) Appl. No.: 17/204,335

(22) Filed: Mar. 17, 2021

(65) Prior Publication Data

US 2021/0293716 A1 Sep. 23, 2021

Related U.S. Application Data

(60) Provisional application No. 63/104,636, filed on Oct. 23, 2020, provisional application No. 63/056,580, filed on Jul. 25, 2020, provisional application No. 62/993,033, filed on Mar. 22, 2020.

(51) Int. Cl.
| | |
|---|---|
| *G01N 21/77* | (2006.01) |
| *G02B 6/42* | (2006.01) |
| *G02B 6/43* | (2006.01) |
| *G01N 33/543* | (2006.01) |
| *B01L 3/00* | (2006.01) |

(52) U.S. Cl.
CPC .... *G01N 21/7703* (2013.01); *B01L 3/502715* (2013.01); *G01N 33/54373* (2013.01)

(58) Field of Classification Search
None
See application file for complete search history.

(56) References Cited

U.S. PATENT DOCUMENTS

| | | | |
|---|---|---|---|
| 4,908,112 A | 3/1990 | Pace | |
| 5,359,681 A * | 10/1994 | Jorgenson | G01N 21/7703 385/127 |
| 5,864,641 A * | 1/1999 | Murphy | G01D 5/35377 385/127 |
| 6,603,548 B2 | 8/2003 | Church et al. | |
| 7,391,936 B2 | 6/2008 | Pau et al. | |
| 7,433,552 B2 | 10/2008 | Kiesel et al. | |

(Continued)

FOREIGN PATENT DOCUMENTS

| | | |
|---|---|---|
| CN | 10873693 A | 3/2020 |
| CN | 111965141 A | 11/2020 |
| WO | WO2020097268 A1 | 5/2020 |

OTHER PUBLICATIONS

Alina Zettner, Ardian B. Gojani, Thomas Schmid and Igor B. Gornushkin, "Evaluation of a Spatial Heterodyne Spectrometer for Raman Spectroscopy of Minerals," MDPI, Feb. 24, 2020, Basel, Switzerland.

(Continued)

*Primary Examiner* — Neil N Turk
(74) *Attorney, Agent, or Firm* — Charles W Gaines

(57) ABSTRACT

This disclosure presents a docking station into which a test card can be inserted for rapid analyte detection and reporting. This docking station has portable capability and can include wire or wireless transmission to a local server or cloud-based server. A test card that has a test structure located on the test structure that includes a modified waveguide can be inserted into the and a docking station that includes a laser and interferometer provides for accurate and rapid detection of a test sample.

18 Claims, 32 Drawing Sheets

(56) References Cited

U.S. PATENT DOCUMENTS

| | | | |
|---|---|---|---|
| 7,630,063 | B2 | 12/2009 | Padmanabhan et al. |
| 8,018,595 | B2 | 9/2011 | Huh et al. |
| 8,216,518 | B2 | 7/2012 | Chau et al. |
| 8,241,487 | B2 | 8/2012 | McCann et al. |
| 8,472,758 | B2 | 6/2013 | Bulovic et al. |
| 9,322,995 | B2 | 4/2016 | Erickson et al. |
| 9,612,197 | B2 | 4/2017 | Chau et al. |
| 9,664,500 | B2 | 5/2017 | Wang et al. |
| 9,766,223 | B2 | 9/2017 | Gourley |
| 10,054,546 | B2 | 8/2018 | Stievater et al. |
| 10,481,348 | B2 | 11/2019 | Song et al. |
| 10,830,936 | B2 | 11/2020 | Menezes et al. |
| 2002/0177135 | A1* | 11/2002 | Doung ............... B01F 33/3033 435/287.2 |
| 2003/0096081 | A1* | 5/2003 | Lavallee ............. B01F 33/30 428/156 |
| 2003/0201462 | A1* | 10/2003 | Pommer ............. G02B 6/4259 257/200 |
| 2005/0232544 | A1* | 10/2005 | Blumberg ........... B82Y 35/00 385/128 |
| 2006/0045809 | A1* | 3/2006 | Shirai ............... G01N 33/54373 422/82.11 |
| 2006/0098926 | A1* | 5/2006 | Shelnut ............. G02B 6/43 385/129 |
| 2006/0164654 | A1* | 7/2006 | Eah ................... B82Y 20/00 356/498 |
| 2007/0211985 | A1* | 9/2007 | Duer ................. G01N 21/253 422/82.11 |
| 2008/0019876 | A1 | 1/2008 | Chau et al. |
| 2008/0267564 | A1 | 10/2008 | Han et al. |
| 2009/0190877 | A1* | 7/2009 | Wang ............... G01N 21/7703 385/12 |
| 2010/0128275 | A1* | 5/2010 | Chau ................ G01N 21/7703 977/954 |
| 2013/0170782 | A1 | 7/2013 | Evans et al. |
| 2014/0094114 | A1* | 4/2014 | Bates ............... G01N 35/00871 455/39 |
| 2016/0334866 | A9 | 11/2016 | Mazed et al. |
| 2017/0268988 | A1 | 9/2017 | Swanson |
| 2018/0126381 | A1 | 5/2018 | Huff et al. |
| 2018/0214863 | A1 | 8/2018 | Sui et al. |
| 2019/0025505 | A1 | 1/2019 | Kraft |
| 2019/0170631 | A1 | 6/2019 | Shachar et al. |
| 2019/0310247 | A1 | 10/2019 | Tak et al. |
| 2019/0336006 | A1 | 11/2019 | Horstmeyer et al. |
| 2019/0360913 | A1 | 11/2019 | Schmidt |
| 2019/0369121 | A1* | 12/2019 | McDevitt ........... G01N 33/6893 |
| 2020/0072828 | A1 | 3/2020 | Chau et al. |
| 2020/0166453 | A1 | 5/2020 | Lendl et al. |

OTHER PUBLICATIONS

Chad G. Atkins, et al., Raman Spectroscopy of Blood and Blood Components, Applied Spectroscopy, 2017, vol. 71(5) 767-793.

Ilokugbe Ettah, et al., Engaging with Raman Spectroscopy to Investigate Antibody Aggregation, Department of Chemnistry, Lancaster University, Lancaster, Lancashire LA1 4YB, UK.

Andrew J. Berger, et al. Multicomponent blood analysis by near-infrared Raman Spectroscopy, Applied Optics, vol. 38, No. 13, May 1999.

Annika M. K. Enejder, et al. , Blood analysis by Raman Spectroscopy, Optics Letters, vol. 27, No. 2, Nov. 15, 2002.

Haiyi Bian, et al., Dual-model analysis for improving the discrimination performance of human and nonhuman blood based on Raman spectroscopy, Biomedical Optics Express 3512, vol. 9, No. 8, Aug. 2018.

Ben Hansson, et al. Development of a flow cell based Raman spectroscopy technique to overcome photodegradation in human blood, Biomedical Optics Express 2275, vol. 10, No. 5, May 2019.

Audrey E. Baker, et al., Raman spectroscopy characterization of antibody phases in serum, nAbs 6:6, 1509-1517, Nov./Dec. 2014.

Nan Li, et al., A Noninvasive Accurate Measurement of Blood Glucose Levels with Raman Spectroscopy of Blood in Microvessels, MOE Key Laboratory of Laser Life Science & Laboratory of Photonic Chinese Medicine, College of Biphotonics, South China Normal University, Guangdon 510631, Chima, Apr. 13, 2019.

Kate L. Bechtel, et al., Intrinsic Raman spectroscopy for quantitative biological spectroscopy Part II, NIH Public Access, 16(17), 12737-12745, Aug. 18, 2008.

Wei-Chuan, et al., Intrinsic Raman spectroscopy for quantitative biological spectroscopy Part I: Theory and simulations, NIH, Public Access, 16(17), 12726-12736, Aug. 18, 2008.

Alexandra V. Soldatova, et al., New Light on NO Bonding in Fe(III) Heme Proteins from Resonance Raman Spectroscopy and DFT Modeling, NIH Public Access, 132(13), 4614-4625, Apr. 7, 2010.

Ishan Barman, et al., Turbidity corrected Raman spectroscopy for blood analyte detection, NIH Public Access, 81 (11), 4233-4240, Jun. 1, 2009.

Ishan Barman, et al., An accurate spectroscopic calibration for non-invasive glucose monitoring by modeling the physiological glucose dynamics, NIH Public Access, 82(14), 6104 6114, Jul. 15, 2010.

Ishan Barman, et al., Raman spectroscopy based sensitive and specific detection of glycated hemoglobin, NIH Public Access, 84(5), 2472-2482, Mar. 6, 2012.

Narahara Chari Dingari, et al., Investigation of the specificity of Raman sepectroscopy in non-invasive blood glucose measurements, NIH Public Access, 400(9), 2871-2880, Jul. 2011.

Anna K. Boardman, et al., Rapid Detection of Bacteria from Blood with Surface-Enhanced Raman Spectroscopy, HHS Public Access, Anal Chem., 88(16), 2026-8035, Aug. 16, 2016.

Rekha Gautam, et al., Non-Invasive Analysis of Stored Red Blood Cells Using Diffuse Resonance Raman Spectroscopy, HHS Public Access, Analyst, 143(24), 5950-5958, Dec. 13, 2018.

Jingwei Shao, et al., In Vivo Blood Glucose Quantification Using Raman Spectroscopy, PLoS ONE 7(10): e48127.

Gunes Acikgoz, et al. Determination of Ethanol Blood Samples Using Partial Least Square Regression Applied to Surface Enhanced Raman Spectroscopy, Toxicological Research, vol. 34, No. 2, pp. 127-132, 2018.

Chang, Y. et. al "Cocaine Detection By A Mid-Infrared Waveguide Integrated With A Microfluidic Chip," 3020-3023. Lab On Chip, 2012, 12.

Dhakal, Ashim, et. al "Evanescent excitation and collection of spontaneous Raman spectra using silicon nitride nanophotonic waveguides," Photonics Resarch Group, INTEC Department, Ghent University, Apr. 28, 2014.

* cited by examiner

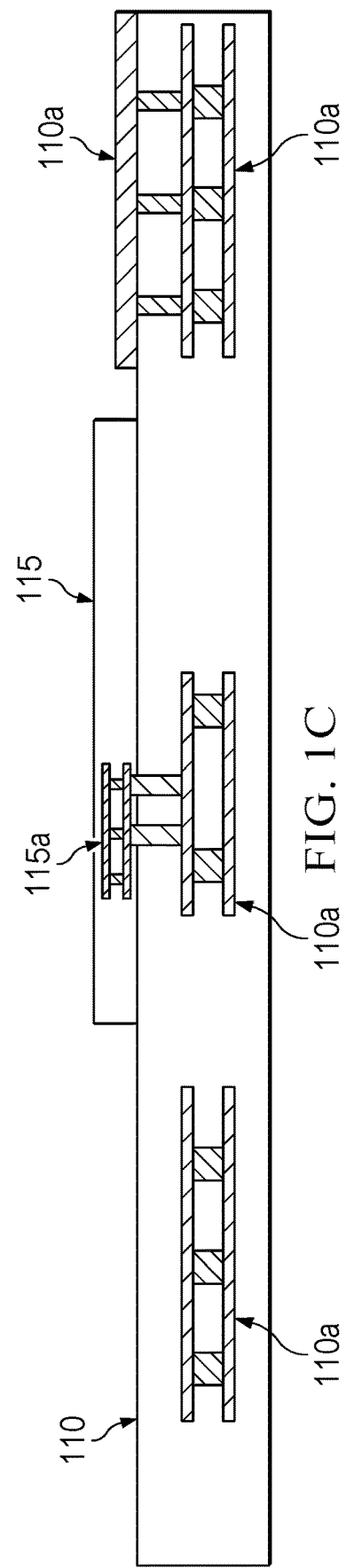

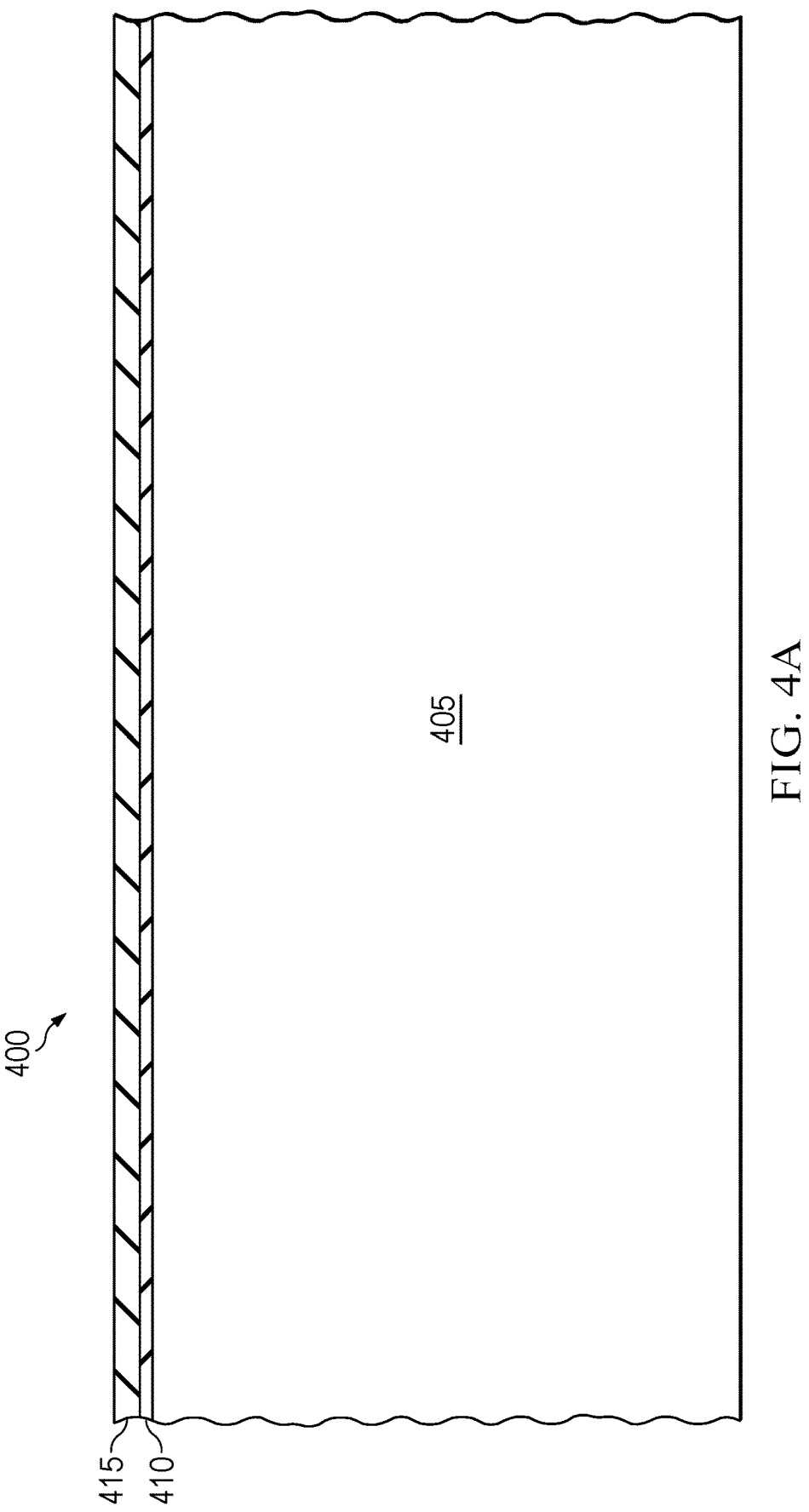

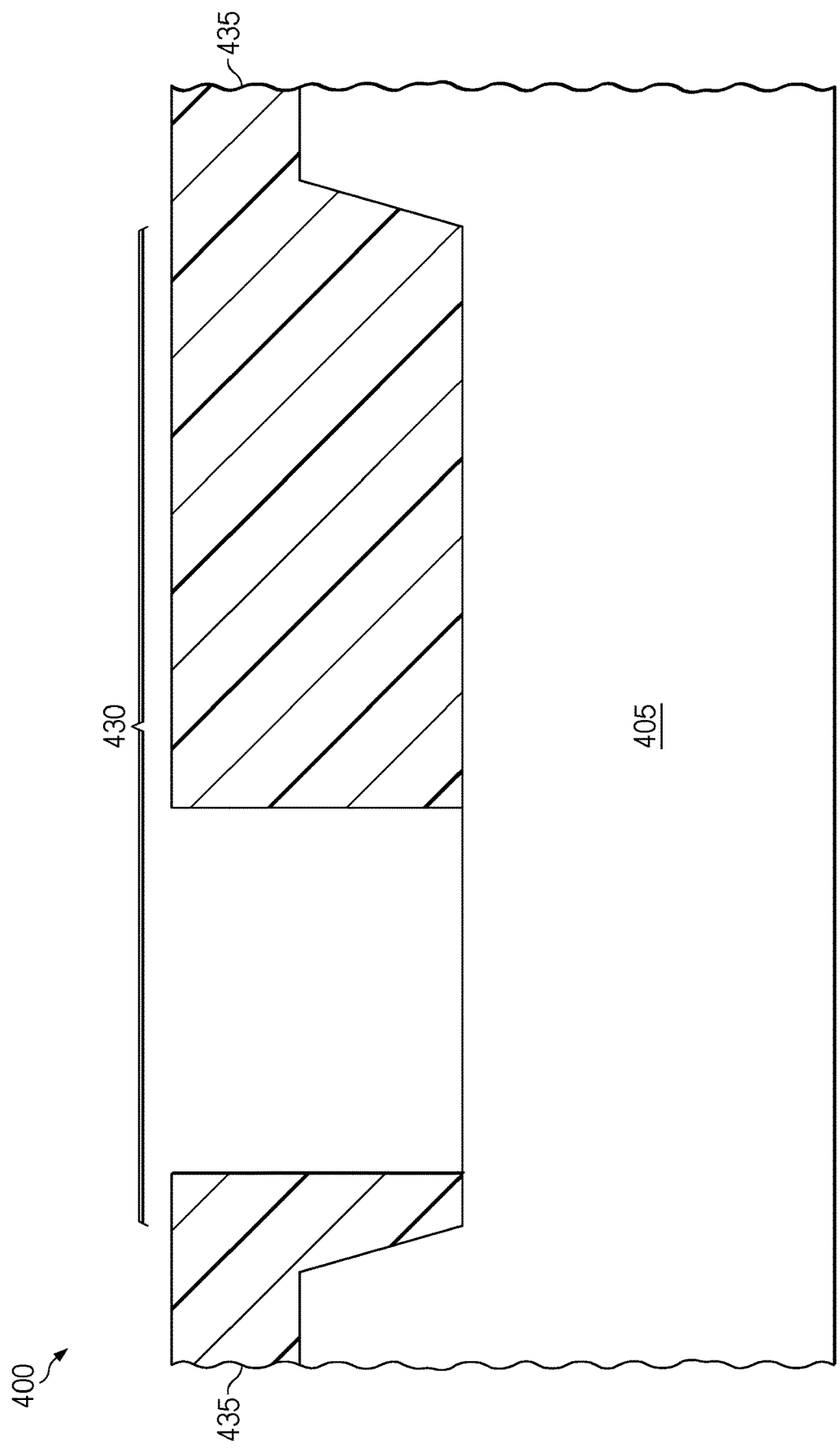

DOCKING STATION WITH WAVEGUIDE ENHANCED ANALYTE DETECTION STRIP

CROSS-REFERENCE TO RELATED APPLICATIONS

This application claims the benefit of U.S. Provisional Application Ser. No. 62/994,200, filed on Mar. 24, 2020, entitled DOCK STATION WITH WAVEGUIDE ENHANCED ANALYTE DETECTION STRIP; U.S. Provisional Application Ser. No. 63/056,580, filed on Jul. 25, 2020, entitled ENHANCED WAVEGUIDE WITH MICROFLUIDIC PUMP; and U.S. Provisional Application Ser. No. 63/104,636, filed on Oct. 23, 2020, entitled DOCKING STATION AND WAVEGUIDE WITH ENHANCED ANALYTE DETECTION STRIP AND OPTICAL AND ELECTRICAL ALIGNMENT SYSTEM, commonly assigned with the present invention and incorporated herein by reference.

TECHNICAL FIELD OF THE DISCLOSURE

The present invention is directed to an optical or photonic device for the rapid detection or presence of an analyte, including analyte pathogens, such as viruses or bacteria, drugs, or cancer cells.

BACKGROUND OF THE INVENTION

With the sudden onset of novel viruses, such as COVID-19, there has arisen an urgent need for rapid detection of possibly infected individuals. Pandemics, such as the very recent COVID-19 virus, has highlighted numerous problems associated with the testing technological response to new and evolving biological threats. Current testing technologies not only face current supply shortages, but they also do not provide a means for quickly obtaining and reporting results. For example, current testing technologies require several days in which to ascertain the presence of a virus. Moreover, if the subject has not been infected for enough time, the test may indicate a false negative, thereby unknowingly causing exposure to the general populous. Current testing technology also lacks the ability to rapidly identify and track mutations. Further, the delayed reporting time causes governmental authorities to lack current data that can be critical in forming and implementing the appropriate policies.

Accordingly, what is urgently needed in the art is a rapid response testing technology that can accurately and quickly determine and report the presence of pathogen in a potentially infected subject.

SUMMARY OF THE DISCLOSURE

To address the above-discussed deficiencies of the prior art, the present disclosure provides a unique, optically based detection technology that provides for accurate measurements and detection that are direct, rapid, and have increased sensitivity in detection of analytes, including human pathogens, such as viruses or bacteria, as well as drugs, other chemicals, or cancer cells. As the covid-19 virus continues to spread, this technology is critical to close the gap between the unacceptably low sensitivity levels and faulty results of current bioassays and the burgeoning need for more rapid and sensitive detection of a wider range of infectious agents with a single platform.

The embodiments as presented herein provide a photonic processing solution with microfluidics and additive manufacturing to implement a compact and surface-enhanced Raman Spectroscopy (SERS) based system to provide rapid viral detection, identification, and reporting solution. These embodiments provide highly accurate, near-real-time, screening and reporting for the presence of any specific pathogen with a device acquisition cost that will permit deployment to any medical facility, public health, and first-responder unit. The Raman spectrum from the SERS interactions is detected using a detector coupled with a Michelson interferometer. The embodiments disclosed herein provide the following: real time remote detection and monitoring of infection; rapid simultaneous identification of the infecting agent, controlled and isolated test protocols limiting the transport or exposure of personnel to contaminated fluids; wireless transmission of data from the test strip to personnel isolated from the test subject; near instantaneous test results; implementation of a test that does not require reagents which can age out or secondary processing of samples; test components which are low cost, easy to manufacture, rapidly deployable and operated with minimal training; and expanded application beyond viral detection.

Embodiments of this disclosure include a docking station into which a test card can be inserted for rapid analyte detection and reporting. This docking station also has portable capability and can include wire or wireless transmission to a local server or cloud-based server.

The foregoing has outlined features so that those skilled in the art may better understand the detailed description that follows. Additional features will be described hereinafter that can form the subject of the claims. Those skilled in the art should appreciate that they can readily use the disclosed conception and specific examples as a basis for designing or modifying other structures for carrying out the same purposes disclosed herein. Those skilled in the art should also realize that such equivalent constructions do not depart from the spirit and scope of the disclosure.

BRIEF DESCRIPTION OF THE DRAWINGS

For a more complete understanding of the present invention, reference is now made to the following descriptions taken in conjunction with the accompanying drawings, in which:

FIG. 1C illustrates a partial sectional view of the test card of FIG. 1B.

FIGS. 4A-4H illustrate partial cross-sectional views of intermediates devices resulting from a process embodiment used to fabricate the microfluidic channel;

DETAILED DESCRIPTION

There is a critical need for systems that provide real time detection and characterization of human viruses. Currently, pathogens, such as the Coronavirus, covid-19, has spread without successful containment due to the combination of long cycle incubation, early non-symptomatic transmission, airborne transmission, and its highly infectious nature. The lack of a simple, rapid, and efficient point of test detection capability, has allowed infected persons to transition from quarantine early or miss quarantine entirely until they became symptomatic. The various embodiments presented in this disclosure addresses these current and urgent needs.

Figure 1A:
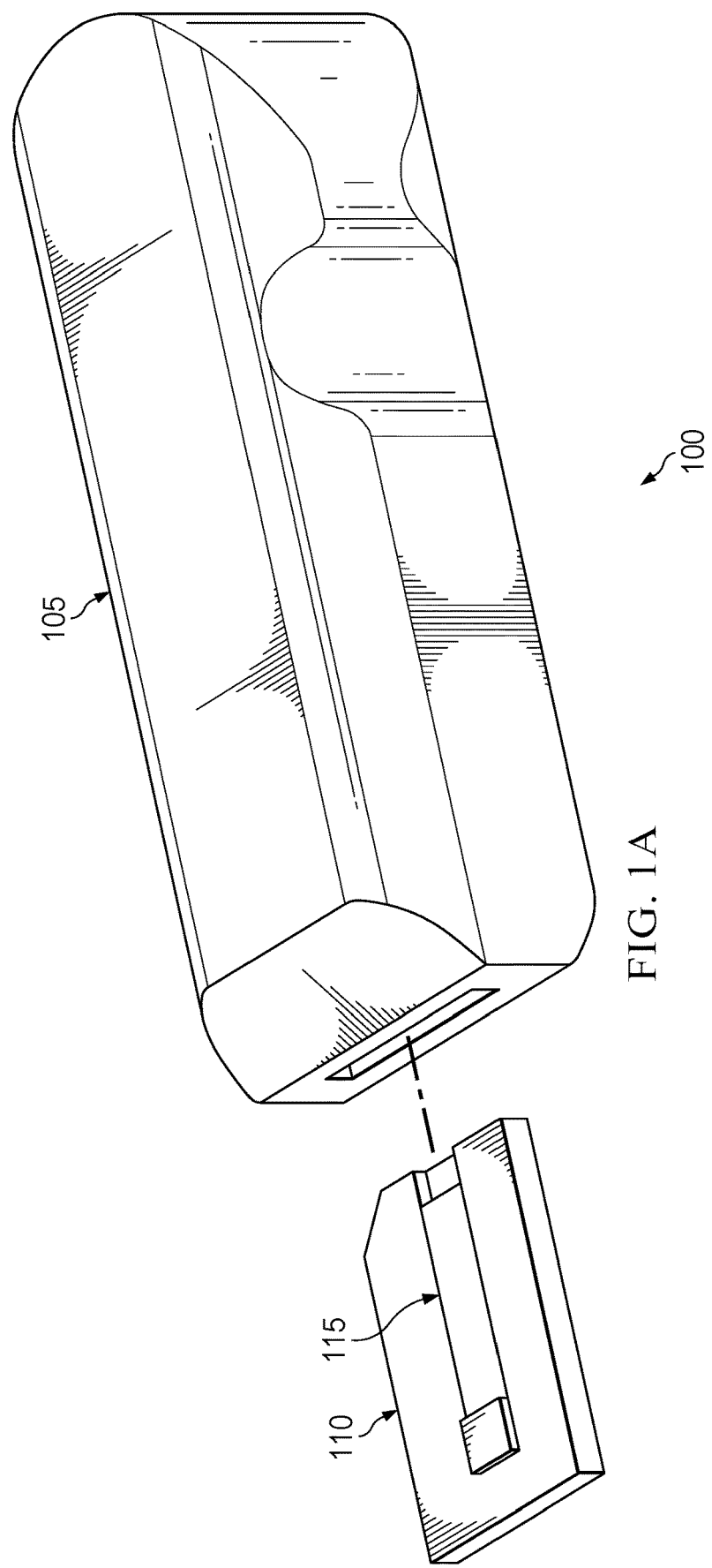
FIG. 1A illustrates an embodiment of a docking station with a test card.

FIG. 1A is a perspective view of an embodiment of a testing apparatus 100 that addresses the above-noted needs. The illustrated embodiment comprises a docking station 105 and test card 110 that is configured to be received within the docking station. A test structure 115 is located on and connected to the test card 110. As explained below, the test structure 115 has a microfluidic channel that provides a fluid path for a fluid or analyte to be tested. The test structure 115 has a modified waveguide formed therein, as described below. The optical waveguide is modified with conductive nanoparticles or nanostructures associated therewith, also explained below. The test sample or analyte is applied to the test structure 115, after which the test card 110 with the test sample is inserted into the docking station 105. Embodiments herein provide optical and electrical alignment systems that allows the optical circuit of the test structure 115, the electronics of the test card 110, and the optical and electrical circuits of the docking station 105 to align to form optical and electrical paths between the test care 110, the test structure, and the docking station 105, as discussed in more detail below. The cooperation between the test card 110 and the docking station 105 provides near instantaneous and accurate test results of the analyte.

Figure 1B:
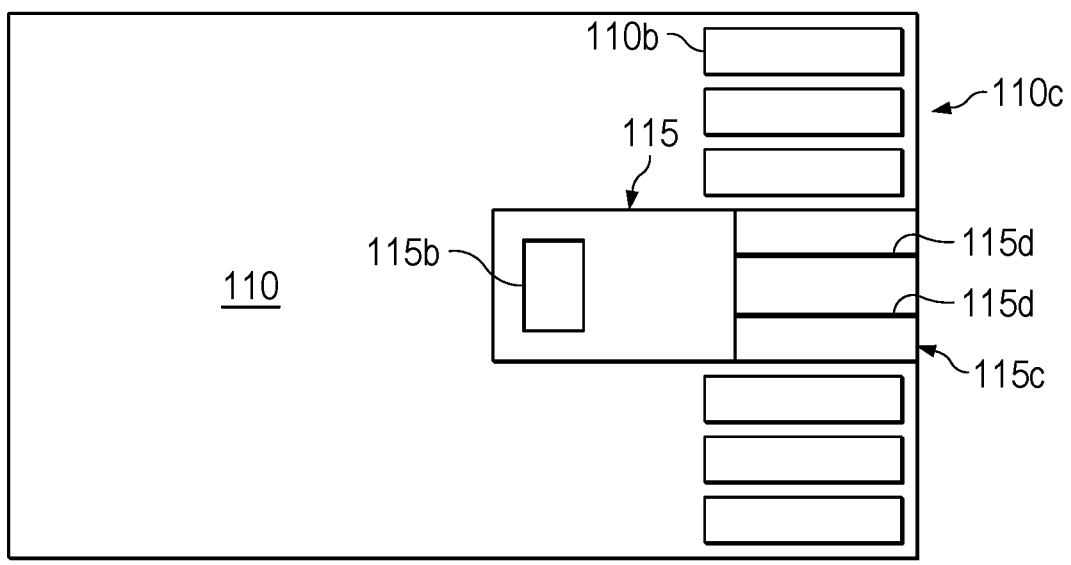
FIG. 1B illustrates an overhead view of an embodiment of a test card configured to be inserted into the docking station.

Proper mechanical alignment of the optical and electrical circuits between the test card 110/test structure 115, and the docking station 105 may be achieved in several ways. For example, in one embodiment, as seen in FIG. 1B and FIG. 1C, which is a general sectional view of FIG. 1B, the test card 110 is a printed circuit board (PCB) that includes one or more metal levels 110a formed between the layers of the PCB. The one or more metal levels 110a are electrically connected to one or more metal levels 115a of the test structure 115, as schematically shown in FIG. 1C. The one or more metal levels 110a, 115a, which may be designed and fabricated using known processes, electrically connect the test structure 115 to electrical lead contacts 110b at an interface end 110c of the test card 110. This embodiment comprises the test structure 115 with a fluid input port 115b that is present in which test fluid may be received therein. As just mentioned, the electrical lead contacts 110b provide electrical connection between the test card 110 and the docking station 105, when the test card 110 is inserted into the docking station 105. Additionally, in an embodiment, the test structure 115 includes an optical output end 115c that includes optical fibers 115d, which may be positioned in V-shaped grooves formed in the substrate of the test structure 115. The optical fibers 115d provide optical coupling between the test structure 115 and the optical components within the docking station 105, while the electrical lead contacts 110b provide electrical connection between the test card 110 and the docking station 105.

Figure 1D:
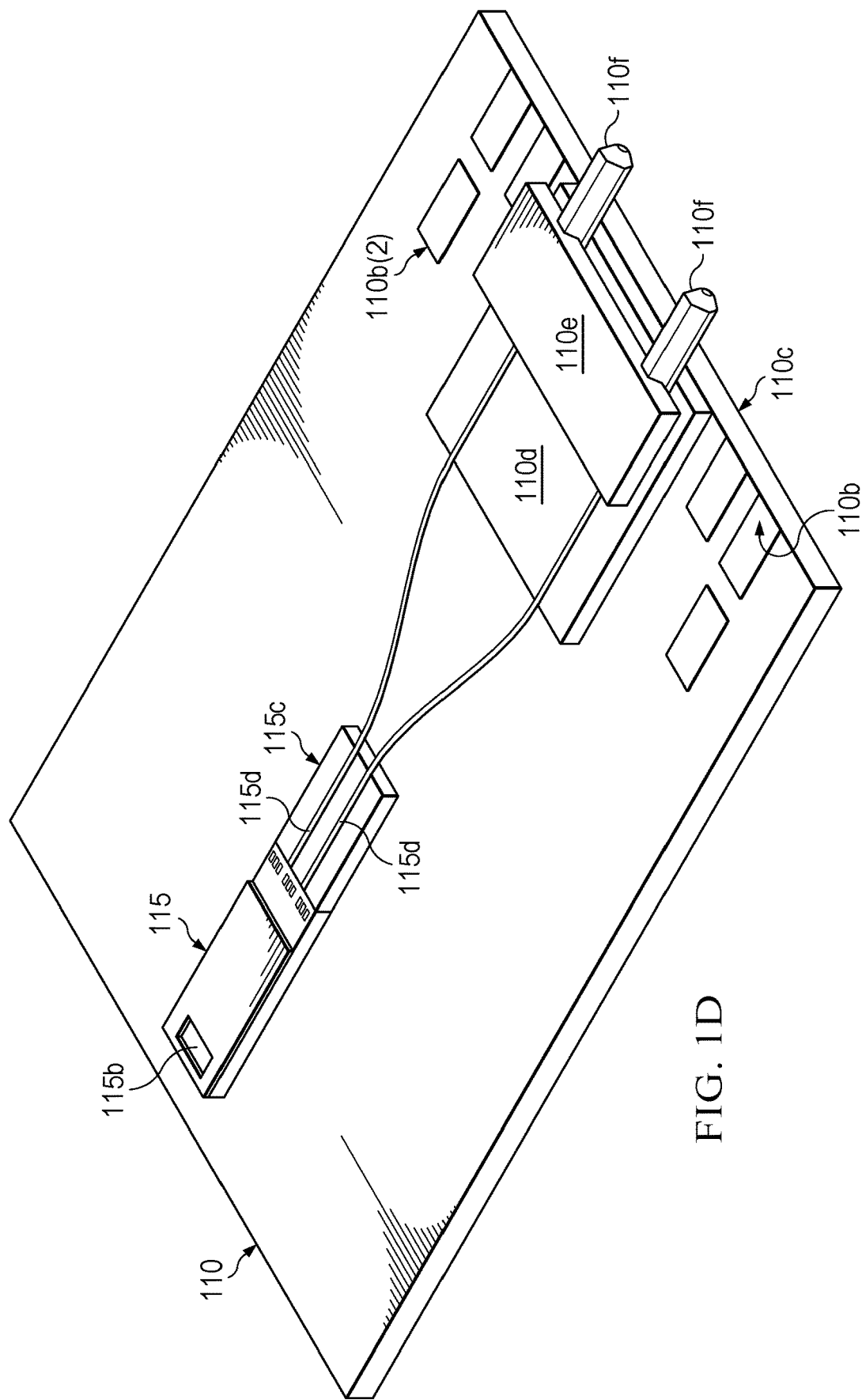
FIG. 1D illustrates a perspective view of another embodiment of a test card configured to be inserted into the docking station.

FIG. 1D illustrates a perspective view of another embodiment of the test card 110 and test structure 115. In this embodiment, the test card 110 includes the electrical lead contacts 110b that provide electrical connection to the electrical circuitry of the docking station 105, FIG. 1A, when the test card 110 is properly inserted in the docking station 105. In certain embodiments, the electrical lead contacts 110b may include grounded leads 110b(2) to prevent electrostatic shorts from occurring. The test structure 115 includes the dual V-Groove optical fibers 115d that extend to a V-Groove fiber mount base 110d, on which is mounted an optical ferrule cap 110e. The optical ferrule cap 110e includes optical ferrules 110f that are spaced apart and through which the optical fibers 115d extend. The optical fibers 115d are optically coupled to the waveguide 205 of the test structure 115. Though only two optical fibers 115d and optical ferrules 110f are shown, other embodiments may include more than the number of optical fibers and optical ferrules that are shown. Though not represented in this view, the above-discussed metal levels within the test card 115 extend from the test structure 115 to the electrical lead contacts 110b to provide electrical connectivity between the test card 110 and the docking station 105, FIG. 1A. When the test card 110 is inserted into the docking station, the optical and electrical leads of the test structure 115 are aligned with or connected to the optical and electrical circuitry of the docking station 105, FIG. 1A.

In the embodiments discussed above, the test structure 115 may be attached to the test card 110 by using known reflow processes to cause the metal levels 110a of the test card 110 to come into electrical contact with the metal levels 115a of the test structure 115.

Figure 1E:
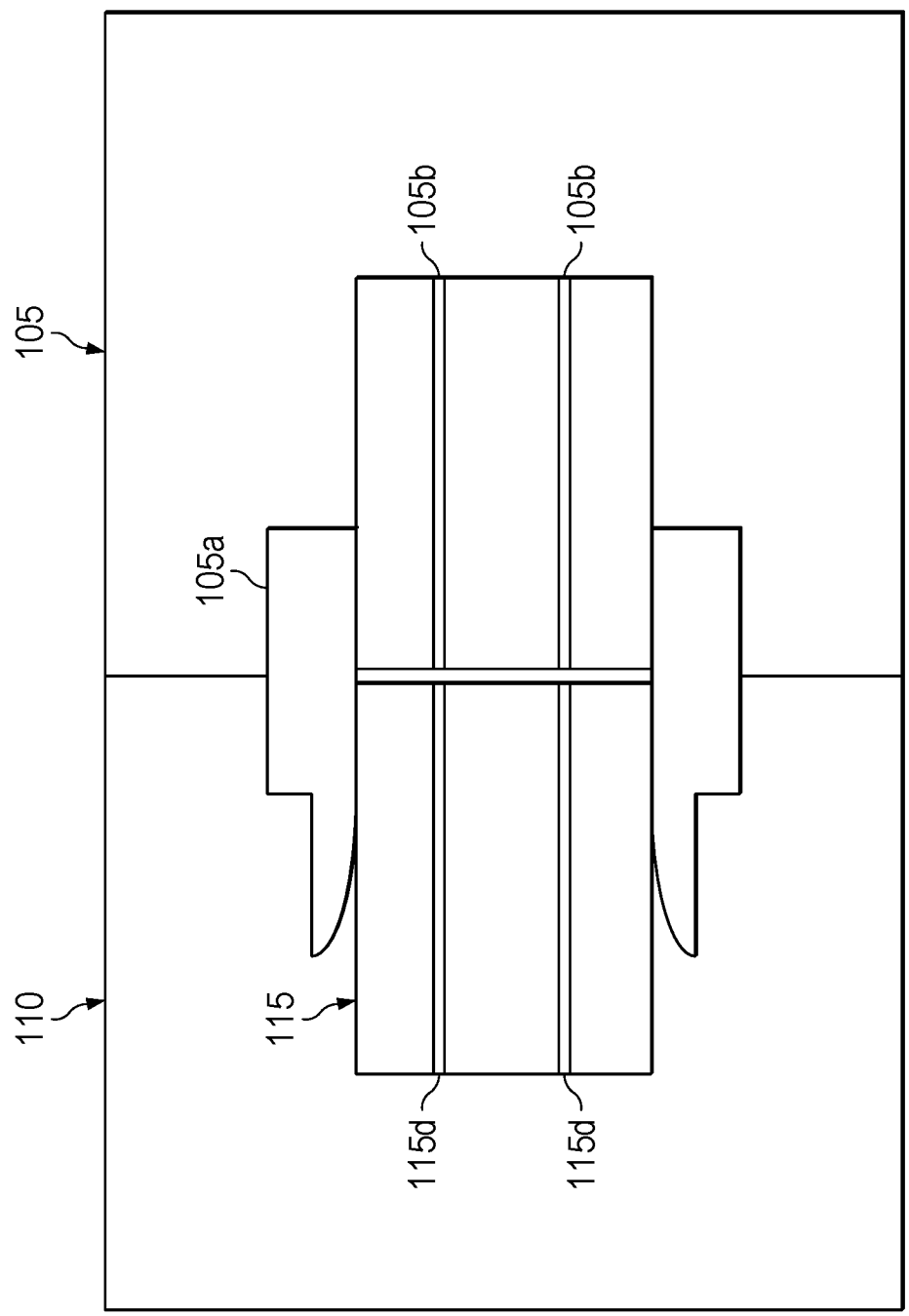
FIG. 1E illustrates an overhead view of another embodiment of a test card inserted into the docking station to achieve optical alignment with the optical circuit of the docking station and to achieve electrical connectivity between the test card and docking station.

FIG. 1E illustrates a partial overhead view of one embodiment wherein the docking station 105 of FIG. 1A, includes a spring biased clip device 105a used to hold the dual V-Groove optical fibers 115d of the test structure 115 in proper optical and electrical alignment with waveguides 105b and electrical circuitry (not shown) of the docking station 105. This embodiment provides high precision placement of the test structure 115 on the test card 110 to reduce alignment complexity, allowing less than 5 microns positional accuracy for the end of the waveguide in the x and z axis. The spring biased clip device 105a not only guides the end of the test structure 115 and test card 110 into optical and electrical connection with the docking station 105, but it holds the test card 110 in place relative with the docking station 105 once engagement is made. In yet another embodiment, alumina may be used on the test card to achieve a smooth surface and known thickness to provide accurate reference for waveguide alignment.

Figure 1F:
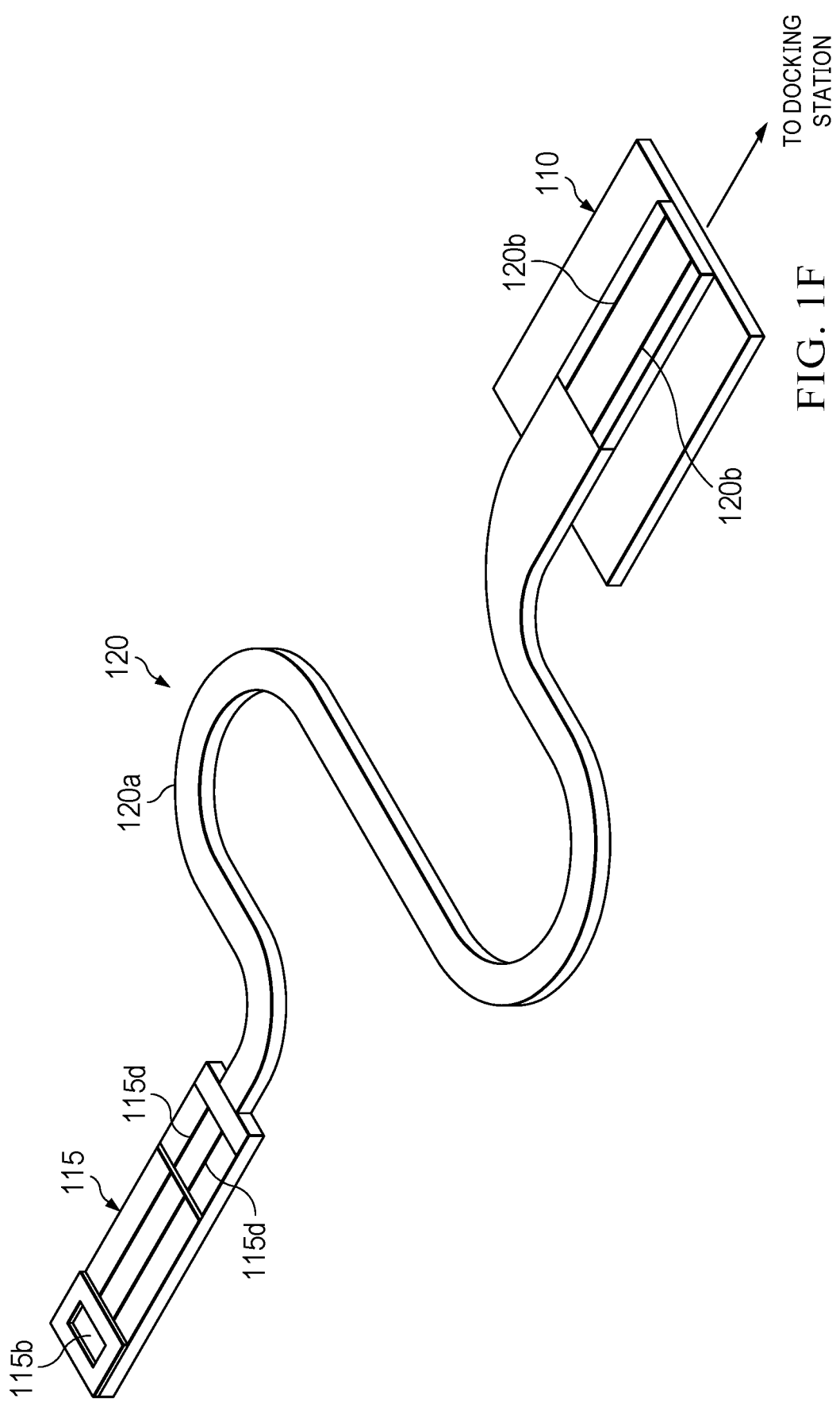
FIG. 1F illustrates a perspective view of a flexible extension sampling strip configured to be coupled to the docking station.

As noted above, the test structure 115 has a fluid sample or input port 115b. However, in some instances, it may be desirable to isolate the person providing the sample to be further isolated from the person administering the test. In such instances and extension test strip configuration may be utilized. FIG. 1F illustrates one such embodiment where the test structure 115 is connectable to a flexible sampling adapter 120 that has optical and electrical paths, not shown, located within a flexible strip 120a. One end of the flexible sampling adapter 120 has corresponding optical V-Grooves and electrical contacts that connect to the test structure 115 and an opposite end that has V-Grooves 120b and electrical contacts that connect to the test card 110, which can then be inserted into the docking station by way of the embodiments described above. When distancing regulations so requires, the flexible sampling adapter 120 allows for more distance of separation when collecting the test sample.

In one embodiment of operation, the test card 110 is placed in the docking station 105 where a calibration cycle will take place to ensure optical alignment between the photonic measurement infrastructure in the docking station 105 and the test structure 115 on the test card 110. Once this calibration is complete, a green LED, or other cue will indicate the test card 110 is ready for sample. A single drop of analyte will be placed on the fluid input or sample port 115b. The sample volume required may be between 0.1 nL and 10 nL. The propagation in the microfluidic channels in test structure 115 are measured by resistance variations in the channel. After the sample is detected, as propagating a target length, a cycle of the dielectrophoretic, at variable frequencies, and Raman spectrum measurements are made to ensure the highest level of accuracy by providing a mechanism to subtract out excess bio-molecule interference if needed, as described above.

Figure 2:
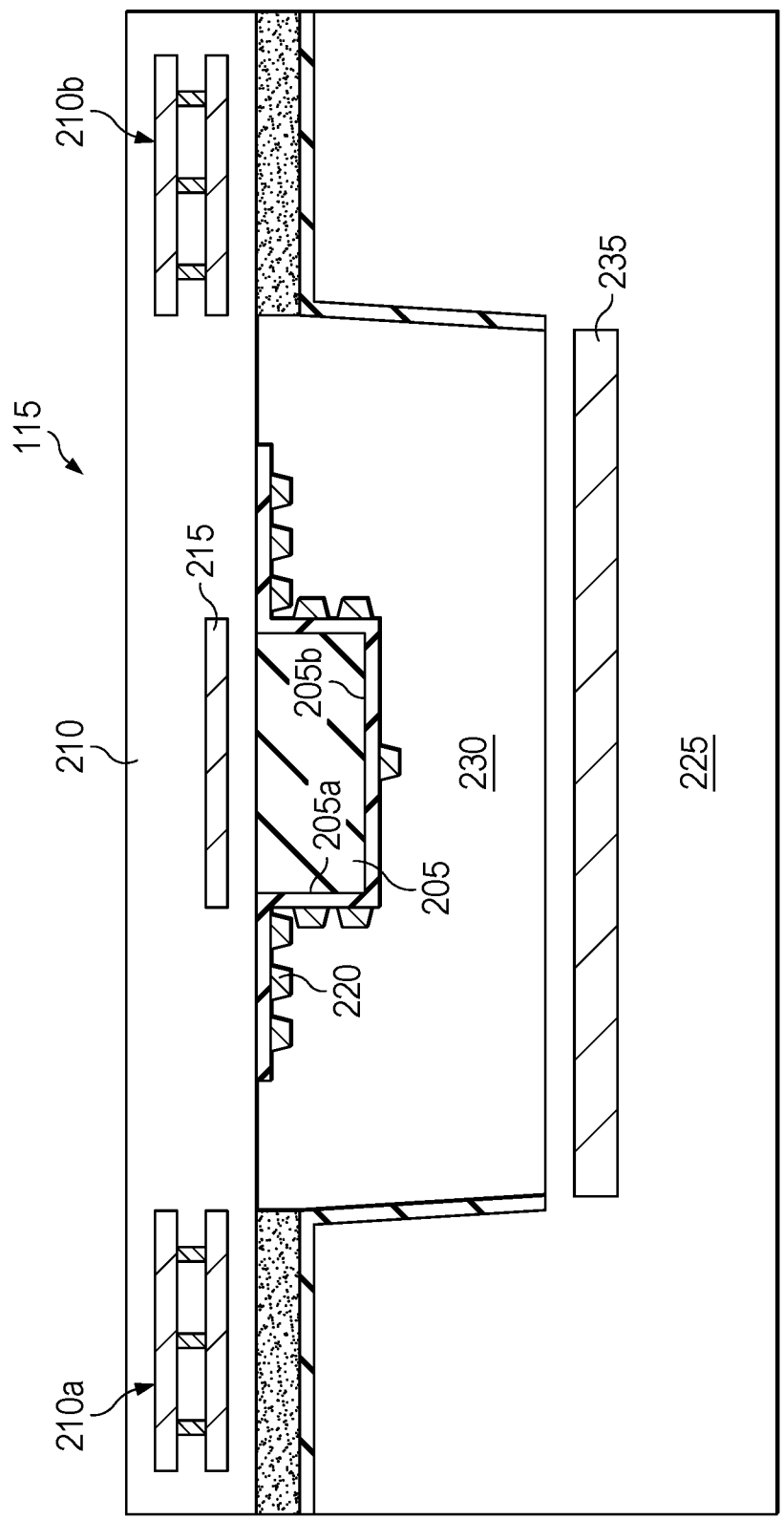
FIG. 2 illustrates a partial sectional view of waveguide of a microfluidic channel of a test card that can be implemented in the dock station.

FIG. 2 illustrates a partial cross-section view of an embodiment of the test structure 115 of the test card 110, as generally shown in FIG. 1. In this embodiment, the test structure 115 includes a waveguide 205 located on a semiconductor substrate 210. The semiconductor substrate 210 may be comprised of a silicon dioxide on a silicon substrate and includes one or more interconnected metal levels 210a, 210b, formed within the silicon dioxide layer. Known lithographic and deposition processes may be used to fabricate the test structure 115. In one embodiment, one of the metal levels 210a, 210b within the semiconductor substrate 210 may include a driving electrode 215 that is one of two electrodes that can be used to form a dielectrophoretic filter (DPF) that can be used to form an electromagnetic field that is perpendicular to the waveguide 205. The DPF is driven by a DPF driver. However, in other embodiments, the driving electrode 215 is optional and thus, may not be present. In one embodiment, the waveguide 205 may be comprised of a silicon nitride material, such as $SiN_2$, $Si_3N_3$, SiON, which can be deposited and etched using known lithographic and deposition processes. Silicon nitride is given as an example, and other types of waveguides may be used, such as Gallium Arsenide, Aluminum Gallium Arsenide, Silicon, Aluminum Oxides, Silicon Oxy-Nitrides, Doped Silicon dioxide (Titanium, Lithium, phosphorus, boron, etc.), or combinations thereof, are also within the scope of this disclosure. The semiconductor substrate 210, metal levels 210a, 210b and waveguide 205, along with the other components discussed below form a unique optical testing circuit.

Nanoparticles 220, such as silver, gold, copper, platinum, palladium, aluminum, or combinations thereof are located on or ("or" as used herein and in the claims includes conjunctive and disjunctive forms, "and/or") adjacent the waveguide 205, that is, the nanoparticles are close enough to shape the charge transfer, or plasmonic resonance of the optical signal being transmitted by the waveguide 205. In one embodiment, the concentration of the nanoparticles 220 may be greater on or adjacent side surfaces 205a of the waveguide 205 than on an outer surface 205b. For purposes herein and in the claims, "outer surface" is the surface that extends the furthest into the depth of the microfluidic channel 230. The nanoparticles 220 extend along a sensor portion of the length of the waveguide 205. The sensor portion is that portion of the waveguide 205 from which test data is collected and used to determine the test results. The sensor portion may extend the length of the waveguide 205 or only a portion of it. In one embodiment, the waveguide 205 has cladded and uncladded portions, wherein the uncladded portions are the sensor portions of the waveguide 205. In such embodiments, the nanoparticles are located on the uncladded portions, whereas in other embodiments, the length of the waveguide 205 may be cladded, and the nanoparticles may be deposited on the cladding along the sensing length of the waveguide 205.

The nanoparticles 220 provide improved data collection as it relates to the test fluid or analyte. Though metals are mentioned specifically, other highly conductive materials that can be deposited or formed at the nanoscale may also be used. For example, a nanostructured semiconductor surface may also be used to shape the charge transfer, or plasmonic resonance as well. Semiconducting materials that have been considered for use include narrow bandgap materials such as silicon carbide, carbon, or gallium nitride as well as narrower bandgap materials such as germanium, lead selenide, lead telluride, Gallium Antimonide, Gallium Arsenide, Indium Phosphide. There are additionally, several evolving semiconductors whose nanostructure behaviors may have unique benefits, such as the chalcoginide molybdenum disulfide ($MoS_2$).

A second silicon substrate 225 is bonded to the semiconductor substrate 210 on the side on which the waveguide 205 is located. The second silicon substrate 225 has a microfluidic channel 230 formed therein. The microfluidic channel 230 encapsulates the waveguide 205, such that the side surfaces 205a and outer surface 205b of the waveguide 205 extend into the microfluidic channel 230, as generally shown. The microfluidic channel 230 provides a channel into which a test fluid or analyte may be placed.

In those embodiments where the driving electrode 215 is present, the second silicon substrate 225 includes a driving electrode 235. Driving electrodes 215 and 235 can be used to produce an additional electrical field to promote controlled transition of the target molecule, such as a pathogen, to the nanostructure surface. As seen in the illustrated embodiment, the driving electrode 215 is located within the semiconductor substrate 210 and adjacent the waveguide 205 and driving electrode 235 is located on the second silicon substrate 225 and within the microfluidic channel 230, as generally shown. The driving electrode 235 may be a metal strip, as shown, in in an alternative embodiment, or it may be formed using a n-type substrate or heavily implanted silicon surface. Driving electrodes 215 and 235 can be used to apply high-frequency (3-5 MHz) voltage to the electrodes for generating a dielectrophoretic (DEP) force within the microfluidic channel 230 to drive the target analytes to the measurement surface.

The DEP may be used to drive biomolecules of a specific mass and size to the measurement surface dramatically enhancing the quantity of the target analyte which will interact with the evanescently guided probe beam. DEP forces can be applied to both conducting and non-conducting particles and can be generated either by using direct current (DC) or alternating current (AC) fields. Dielectrophoretic forces achieves a highly accurate classification of viruses. The DEP force is a force exerted on a suspended particle in the presence of a non-uniform electric field. The magnitude and direction of the force are related to the electric field intensity, particle radius, permittivity of the particle and suspending fluid, as well as the conductivity the particle and suspending fluid. DEP offers the controllable, selective, and accurate manipulation of target viruses.

As known, DEP is the movement of a particle in a non-uniform electric field due to the interaction of the biomolecule's dipole and spatial gradient of the electric field. The biomolecule dipole primarily originates from two phenomena. 1) The permanent dipole due to the orientation and configuration of the atoms, and 2) The induced dipole resulting from the application of an external electric field which introduces a re-distribution of charge on the particle's surface.

The behavior of the biomolecule can be described by its polarizability, the measure of the ability of a material to produce charge at the interface. Its polarizability is the measure of the ability of the material to respond to an electric field, which has three basic mechanisms, namely (i) electronic polarization, (ii) atomic polarization and (iii) orientation polarization.

Interfacial polarizability is limited since it is the origin of the induced dipole on particles within the operating frequencies of 10 kHz to 100 MHz. If the polarizability of the particle is higher than that of the medium, more charges will accumulate at the particle's side. If the polarizability of the medium is higher than that of the particle, more charges will accumulate at the medium's side. This non-uniform distribution of the charges means a difference in the charge density on either side of the particle which leads to an induced dipole across the particle aligned with the applied electric field. When the particle-medium system is placed in a non-uniform electric field, the particle feels different forces at each end. The difference in force at both ends generates a net force in either direction depending on the polarizability of the particle and the medium.

Common practice for application of alternating current dielectrophoresis AC-DEP is an array of metal electrodes embedded inside the microchannel network. Most of the time, these internal electrodes are planar (2-D) ones (i.e., height of the electrodes are in the order of hundred nanometers) are fabricated within the device. AC-DEP is advantageous due to the low operating voltage that prevents Joule heating. Moreover, the lower applied voltages simplify the circuitry required to generate the electric fields, making AC-DEP focused systems compatible with integrated circuits and suitable for battery powered hand-held devices.

Thus, DEP enhances viral detection technology, enhancing or enriching the quantity of selective viral analytes deposited on the measurement surface. Alternative, other embodiments may employ variable frequency and phase selective dielectrophoresis to separate biomolecules by size and structure to allow selective, simultaneous, characterization and identification of a multiplicity of analytes within the same test structure.

Figure 3A:
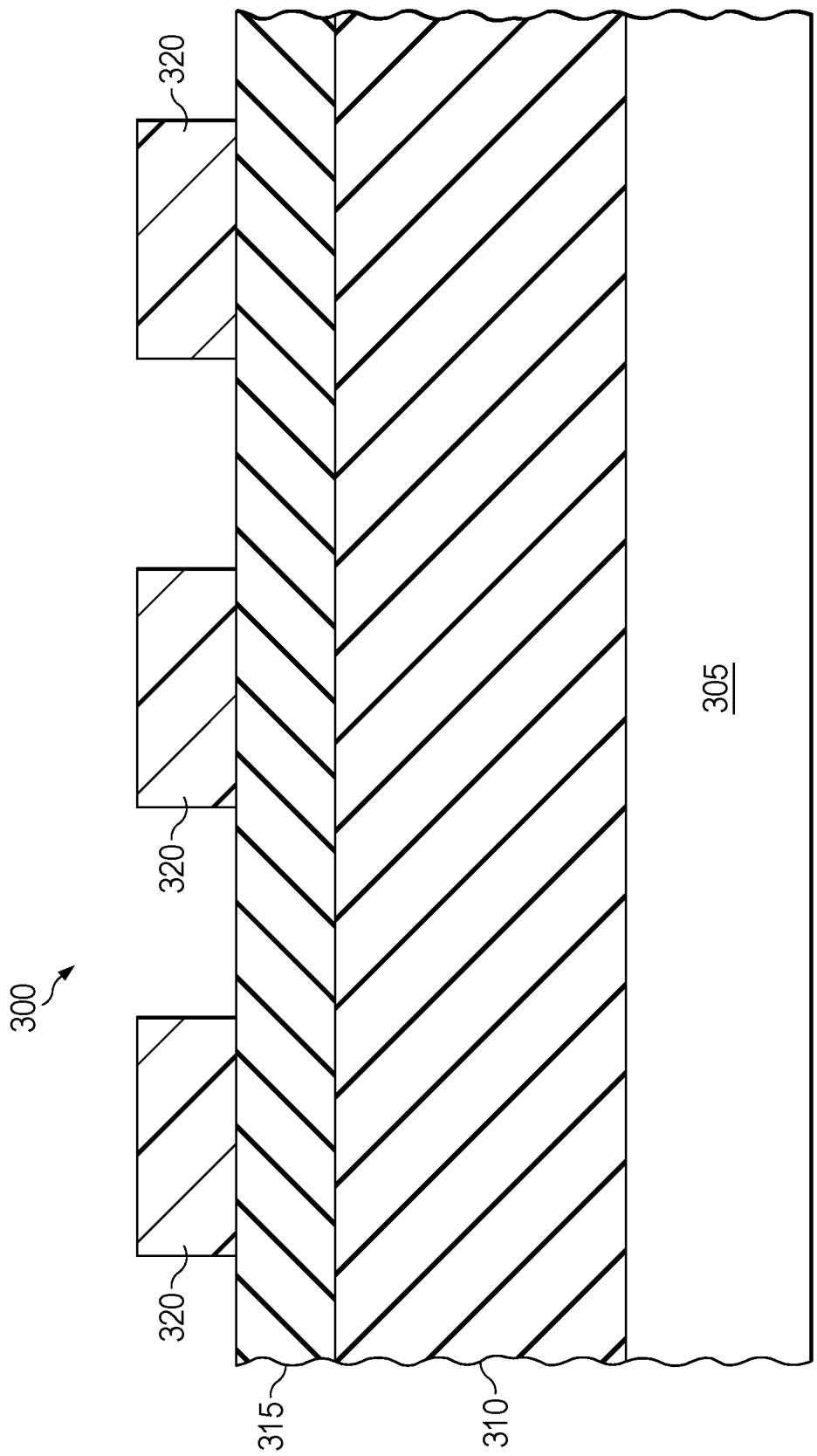
FIGS. 3A-3I illustrate partial cross-sectional views of intermediate devices resulting from a process embodiment used to fabricate the waveguide of the test structure.

FIGS. 3A-3I illustrate partial cross-sections of intermediate structures 300 of one embodiment of a process that can be used to fabricate a plurality of the waveguide 205 of the test structure 115. FIG. 3A illustrates a silicon substrate 305 on which a silicon dioxide layer 310 has been grown. Also seen are a silicon nitride layer 315 and a patterned photoresist layer 320 located on the silicon nitride layer 315. Known processes and materials may be used to form this illustrated intermediate structures and those hereafter discussed. The silicon substrate 305 may be a 200 mm silicon wafer doped with a P-type dopant, depending on the embodiment, the dopant concentration and thickness may vary. In one embodiment, the silicon dioxide layer 310 may be formed to a thickness of 2000 nm. The thickness of the silicon nitride 315 layer that will be later patterned to form the waveguides may also vary. In certain embodiments, the thickness may range from about 100 nm to about 200 nm. In one embodiment, a dry etch may be used to etch the unmasked portions of the silicon nitride layer 315 to produce waveguides having a spacing, that may vary, depending on design requirements. For example, in one embodiment, the spacing between the etched waveguides may be about 300 nm.

Figure 3B:
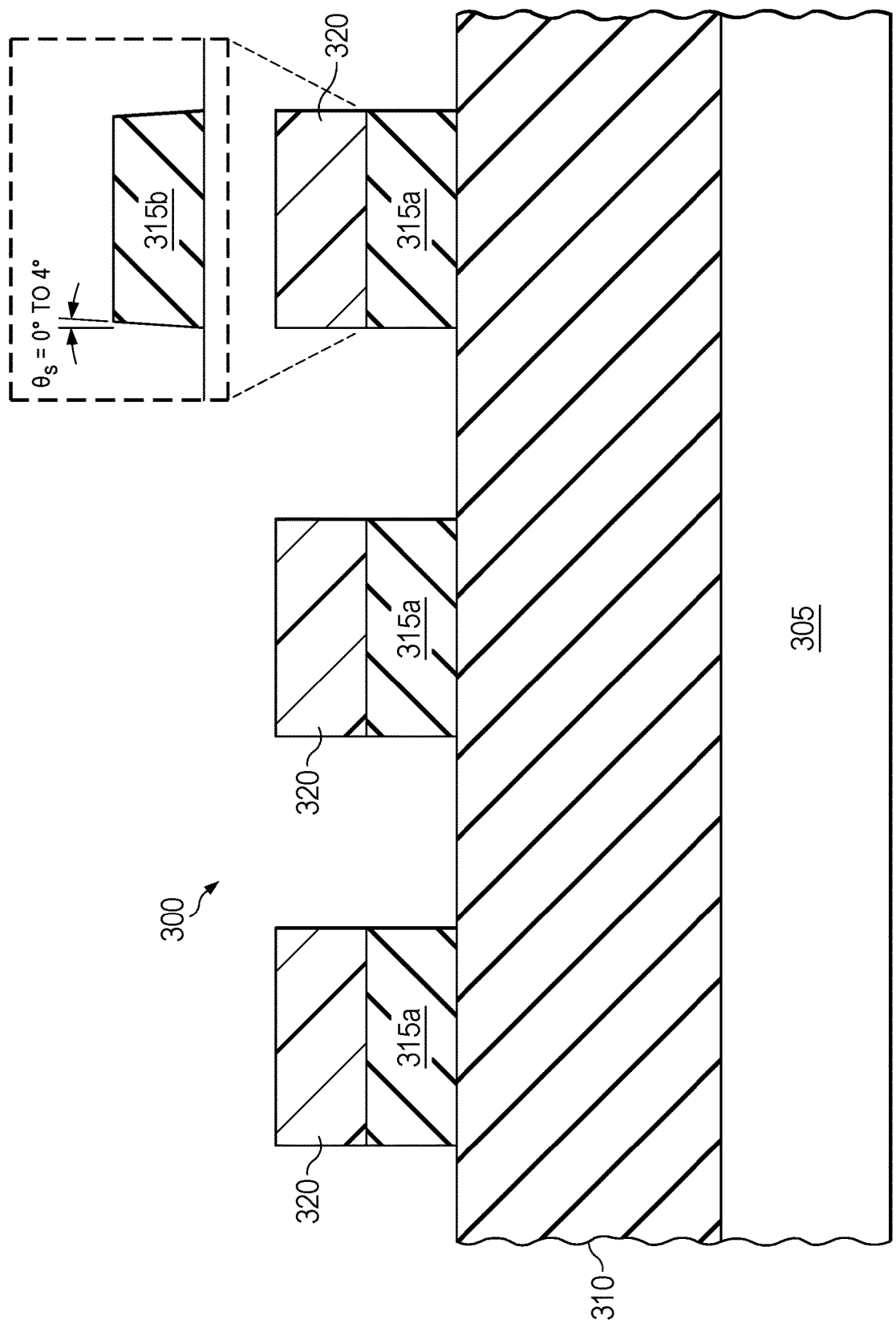
Figure 3C:
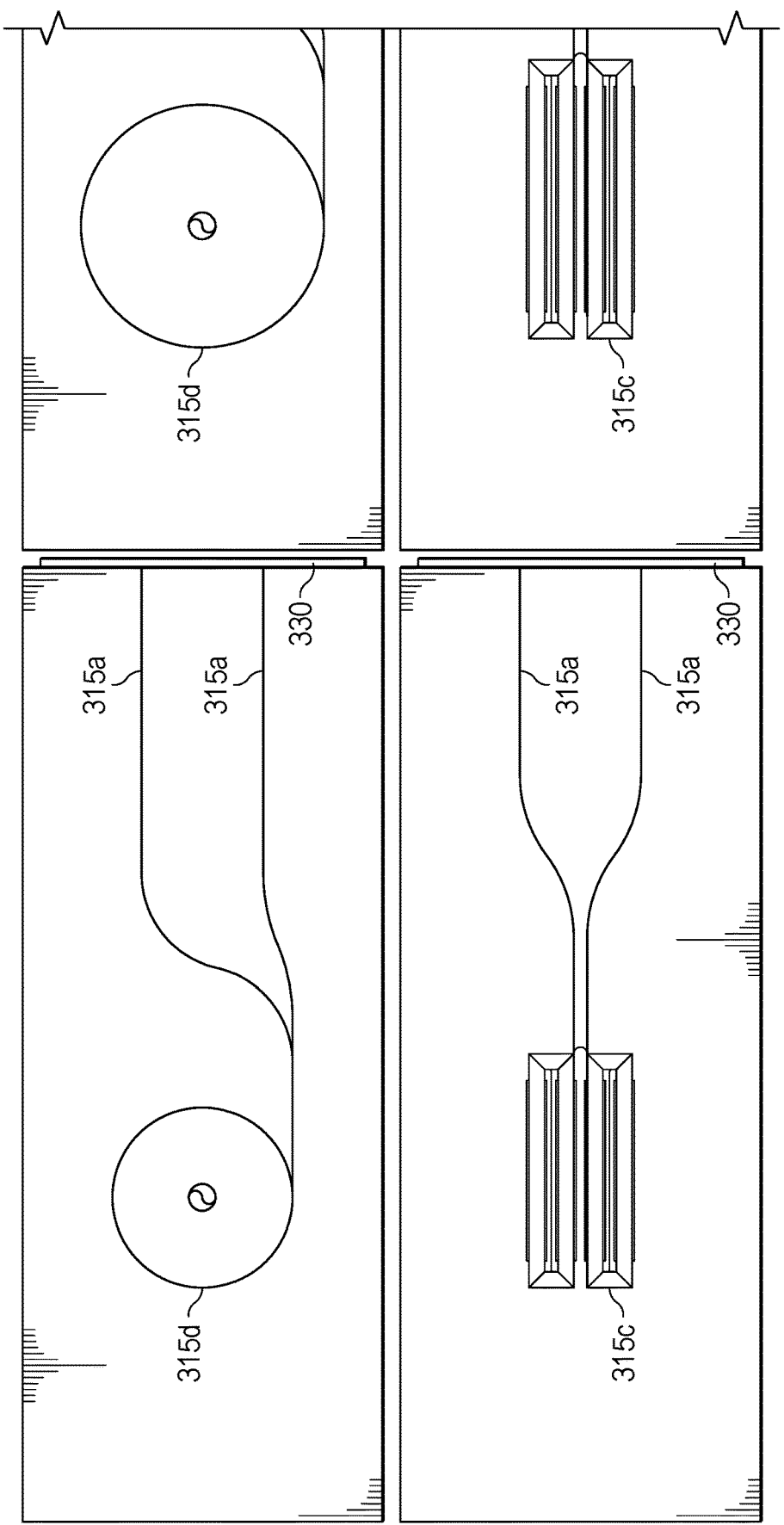
Figure 3D:
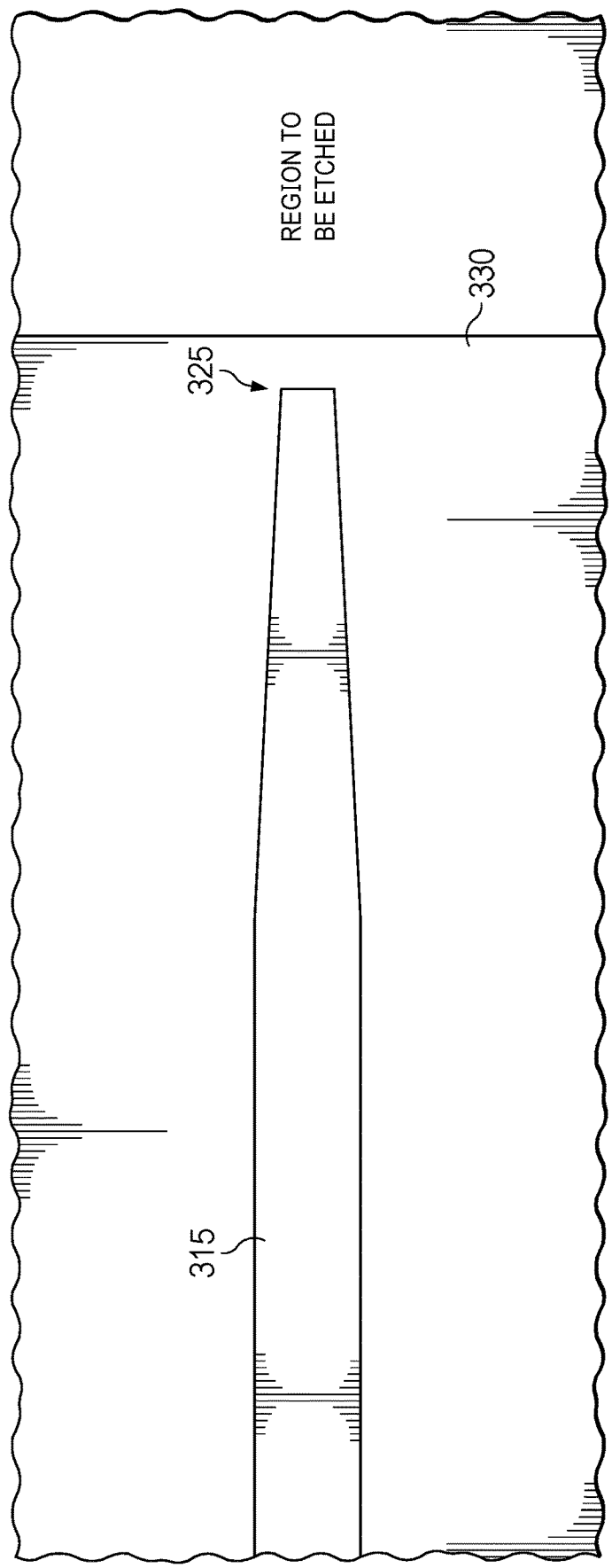

FIG. 3B illustrates the intermediate embodiment of the device shown in FIG. 3A, following the patterning of the silicon nitride 315 to form a plurality of waveguides 315a. In one embodiment a known dry etch may be used to form the waveguides 315a. As shown in an enlarged view 315b of one of the waveguides 315a, the dry etch may cause the edges of the waveguides to taper from about 0° to about 4°. The tapered edges of the waveguides 315a help to further shape the charge transfer or plasmonic resonance. Following the dry etch, the remaining photoresist 320 is removed from the waveguides 315a using known processes, such as strip resist and wafer clean processes. In some embodiments, the waveguides 315a may be patterned into various serpentine geometric designs to increase their lengths. For example, FIG. 3C illustrates a couple of examples in which the waveguides 315a may be patterned in a rectangular folded or serpentine configuration 315c, or a circular configuration 315d. These are presented as only as a couple of examples, and other geometric designs are also within the scope of this disclosure. Additionally, during the patterning of the photoresist, the same reticle can be used to form a tapered region 325 (as seen in FIG. 3D) near an etched facet surface 330. This narrowed tapered region 325 provides for improved modal and optical transmission near the output end of the waveguides. In one embodiment, a deep etch may be conducted to define an optical facet surface at the end of the silicon nitride waveguide 315, as seen in FIG. 3D. This optional etch would be conducted to etch through the underlying silicon oxide and then 2-3 microns into the silicon. In such embodiments, a follow on wet clean may be required to obtain a smooth oxide surface.

Figure 3E:
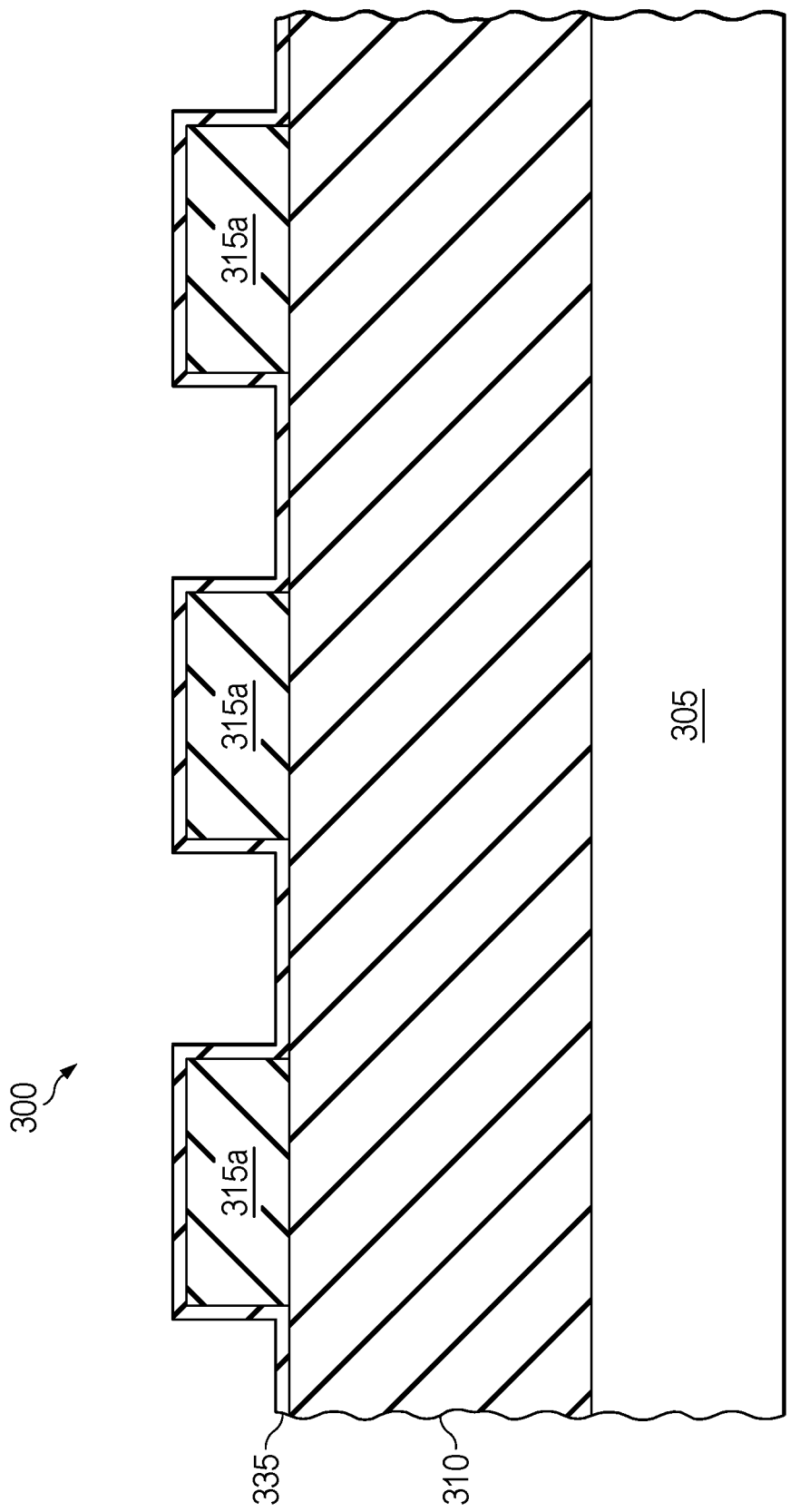

FIG. 3E illustrates the device of FIG. 3B following the removal of the remaining photoresist 320 and the deposition of a nitride etch stop 335 that provides etch control for a subsequent wet etch process. Known deposition processes may be used to deposit the nitride etch stop 335 and may be deposited to a thickness ranging from about 20 nm to about 30 nm. The nitride etch stop 335 provides etch control for a wet etch that is used to expose sensor portions of the waveguides, as shown below. In one embodiment this nitride etch stop 335 remains on the waveguides and serves to expand the waveguide transmission capacity. The nitride etch stop 335 provides etch control for a wet etch that is used to expose sensor portions of the waveguides, as shown below. In one embodiment the nitride etch stop 335 remains on the waveguides 315a and serves to expand the waveguide transmission capacity, which further enhances data collection from the analyte.

Figure 3F:
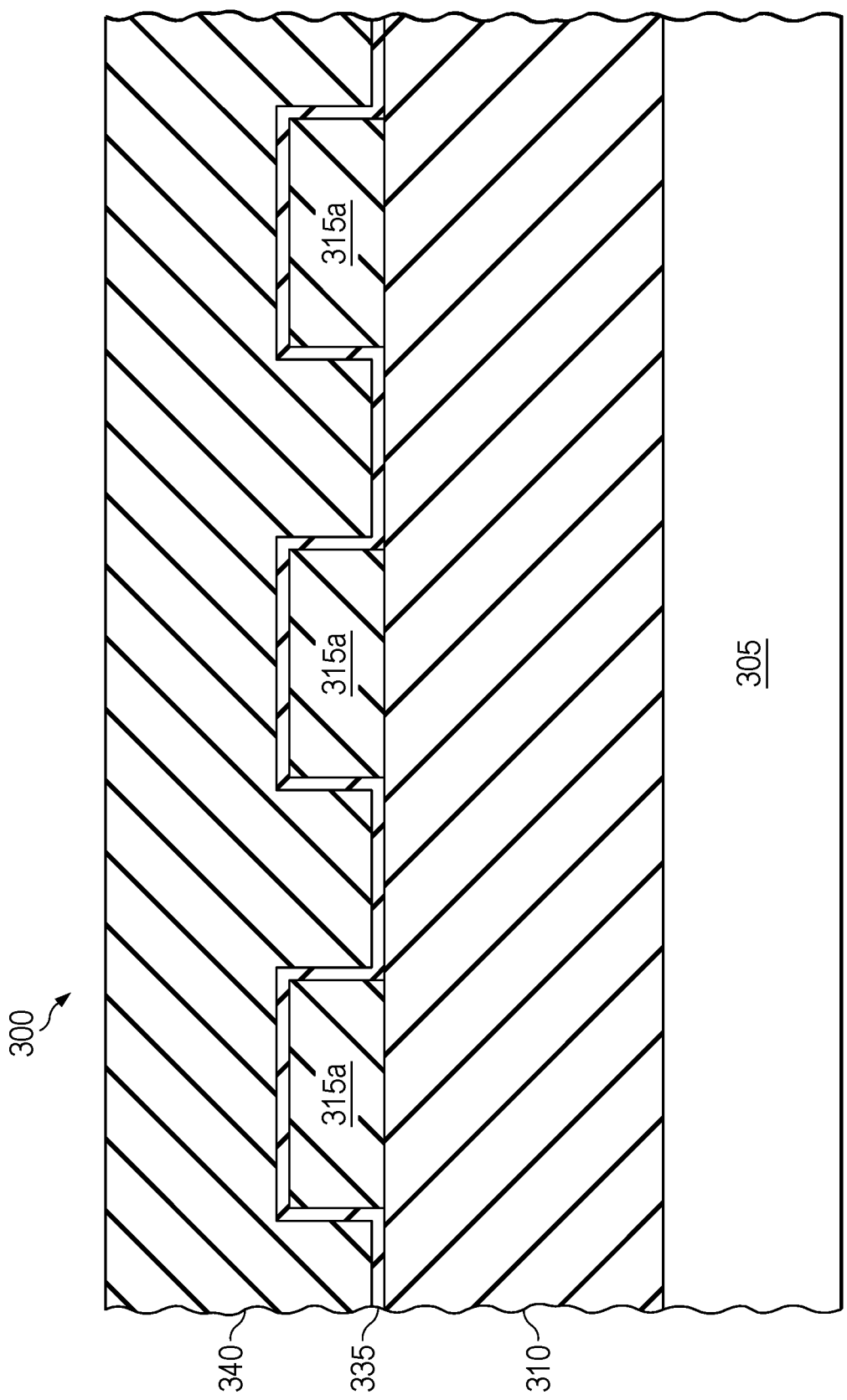

FIG. 3F illustrates the intermediate device of FIG. 3E after the deposition of a silicon oxide layer 340, using known deposition processes. The thickness of the silicon oxide layer 340 may vary, but in one embodiment, the thickness may be about 2 microns. Also, the silicon oxide layer 340 serves as a cladding layer for at least a portion of the waveguides 315a, as explained below.

Figure 3G:
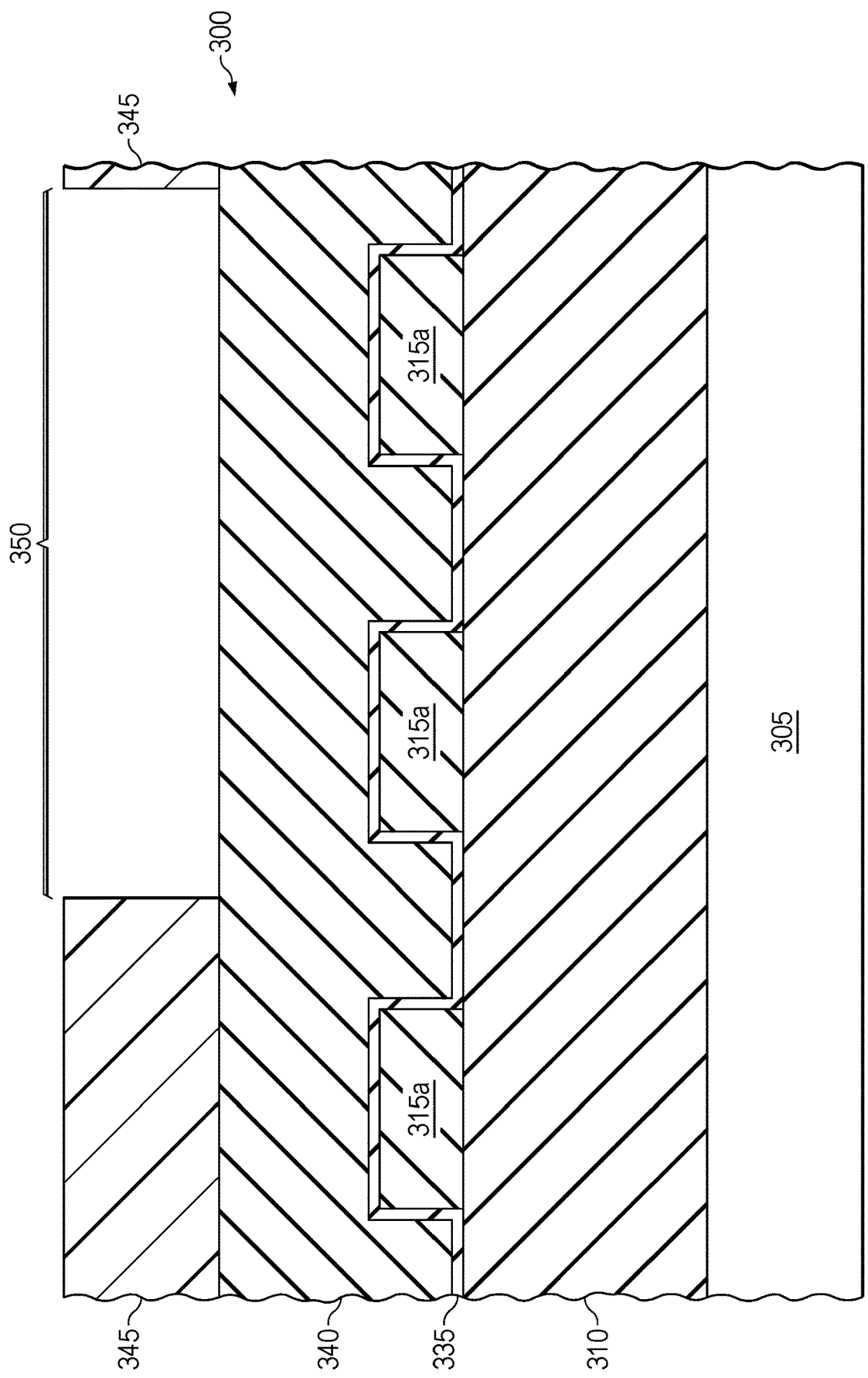
Figure 3H:
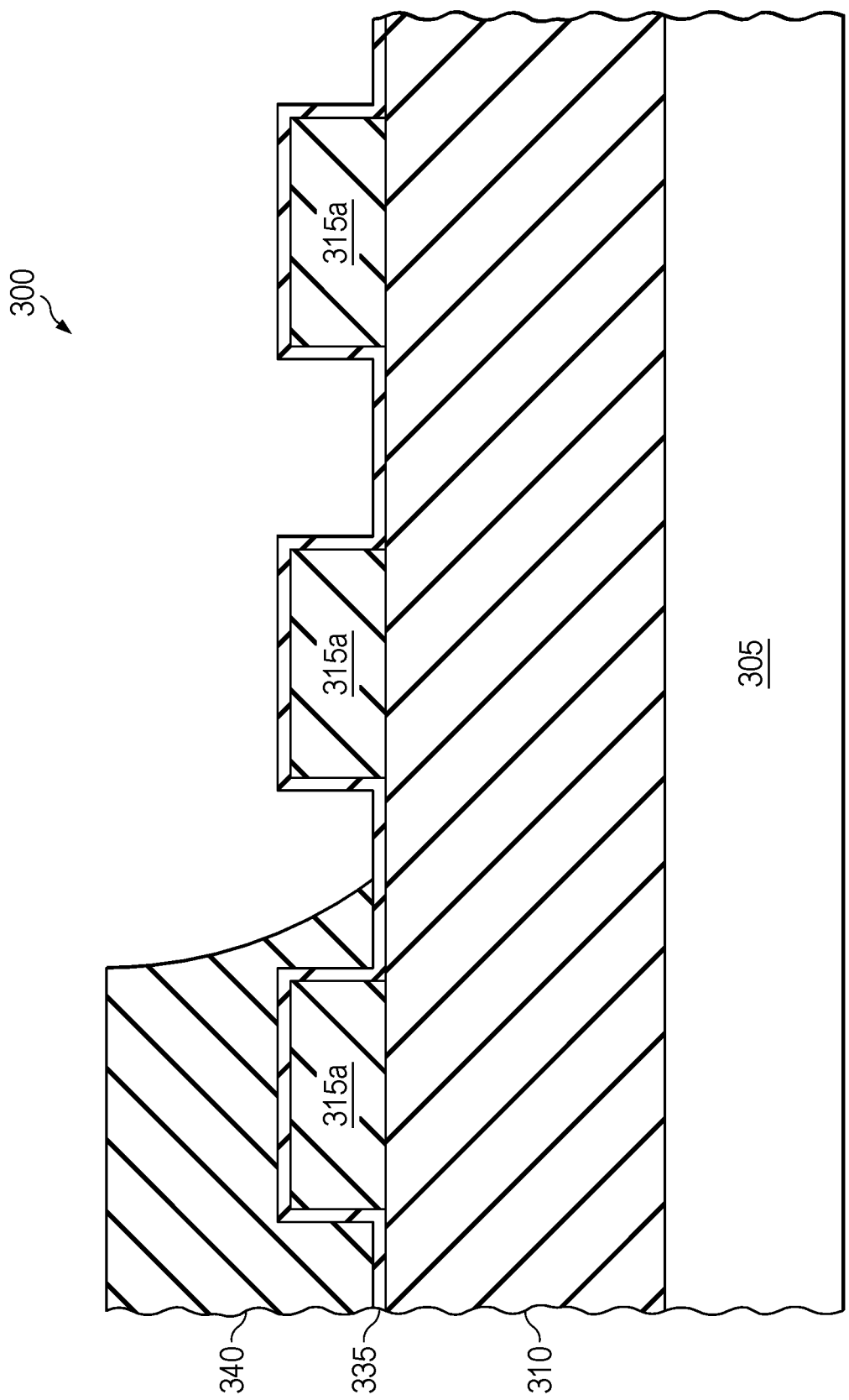

FIG. 3G illustrates the intermediate device of FIG. 3F after the deposition and patterning of a photoresist 345 to form a sensor opening 350 in the photoresist 345. The sensor opening 350 exposes a region of the silicon oxide 340 to a subsequent etch that will remove the silicon oxide from portions of the waveguide, resulting in uncladded waveguides 315a on which the nanoparticles will be deposited and used to collect data from the subject analyte. A known basic wet oxide etch may then be conducted to remove the silicon oxide cladding over targeted waveguides, which results in the intermediate structure, as seen in FIG. 3H. As shown in FIG. 3H, a portion of the waveguides 315a remains cladded by the silicon dioxide 340 while another portion is uncladded and that will serve as sensors to collect data from the subject analyte. These uncladded portion serve as sensor regions that are used to collect data regarding the subject analyte.

Figure 3I:
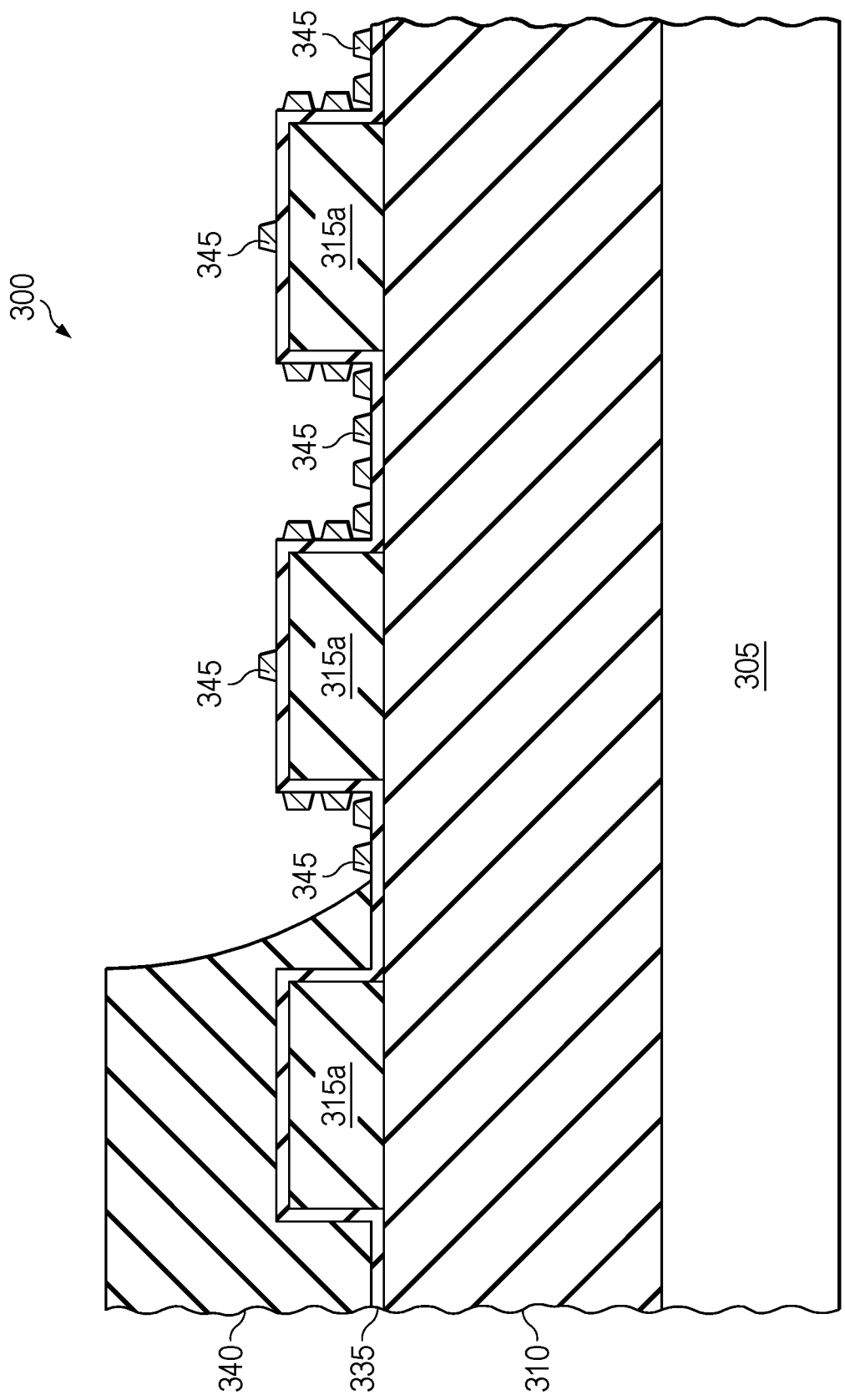

FIG. 3I illustrates the intermediate structure, as seen in FIG. 3H, after the formation of the nanostructures 355 on the exposed waveguides 315a. In some embodiments, the nanostructures 355 may have a diameter that ranges from about 70 nm to about 100 nm on about 140 nm to 300 nm pitch. However, other ranges and pitches can be used to optimize the performance of the device. Different deposition processes may be used to form the nanostructures. For example, in one embodiment, the nanostructures 355 may be deposited using an inkjet deposition processes. In another embodiment, the nanostructures 355 may be used using deep ultraviolet (DUV) photolithography or e-beam lithography with metal deposition liftoff In such embodiments, the thickness of the liftoff structures may range from about 40 nm to about 80 nm, depending on the mean diameter.

FIGS. 4A-4H illustrate partial cross-sections of intermediate structures 400 of one embodiment of a process flow for fabricating the above-mentioned microfluidic channel 230 in a wafer that is ultimately bonded to the wafer on which the waveguide 205 is formed. Once bonded together, the microfluidic channel 230 forms a sealed fluidic channel around the side surface and outermost surface of the waveguide(s), as seen in FIG. 2. In one embodiment, the microfluidic channel 230 comprises two levels, a shallow etched structure, and a deeper etched structure, as discussed below. The shallow etch supports lateral capillary flow, while the deeper etch structure provides vent and feed ports that are exposed during a post back-side grind.

FIG. 4A illustrates a wafer 405, which, in one embodiment, may be a 200 mm silicon wafer that is doped with a known P-type dopant, whose concentration and diffusion depth may vary depending on optimized design requirements. A oxide 410 is formed over the silicon wafer 405 using known process, such as oxidation growth or deposition processes. The thickness of the oxide layer 410 may wavy. For example, the thickness may be about 100 nm or 30 nm to 50 nm under wet etch conditions. A silicon nitride layer 415 is located over the oxide layer 410, and in certain embodiments, its thickness may be about 300 nm. The silicon nitride layer 415 is the hard mask feature for the shallow trench etch. The oxide layer 410 provides isolated removal of the silicon nitride 415 layer in subsequent steps.

Figure 4B:
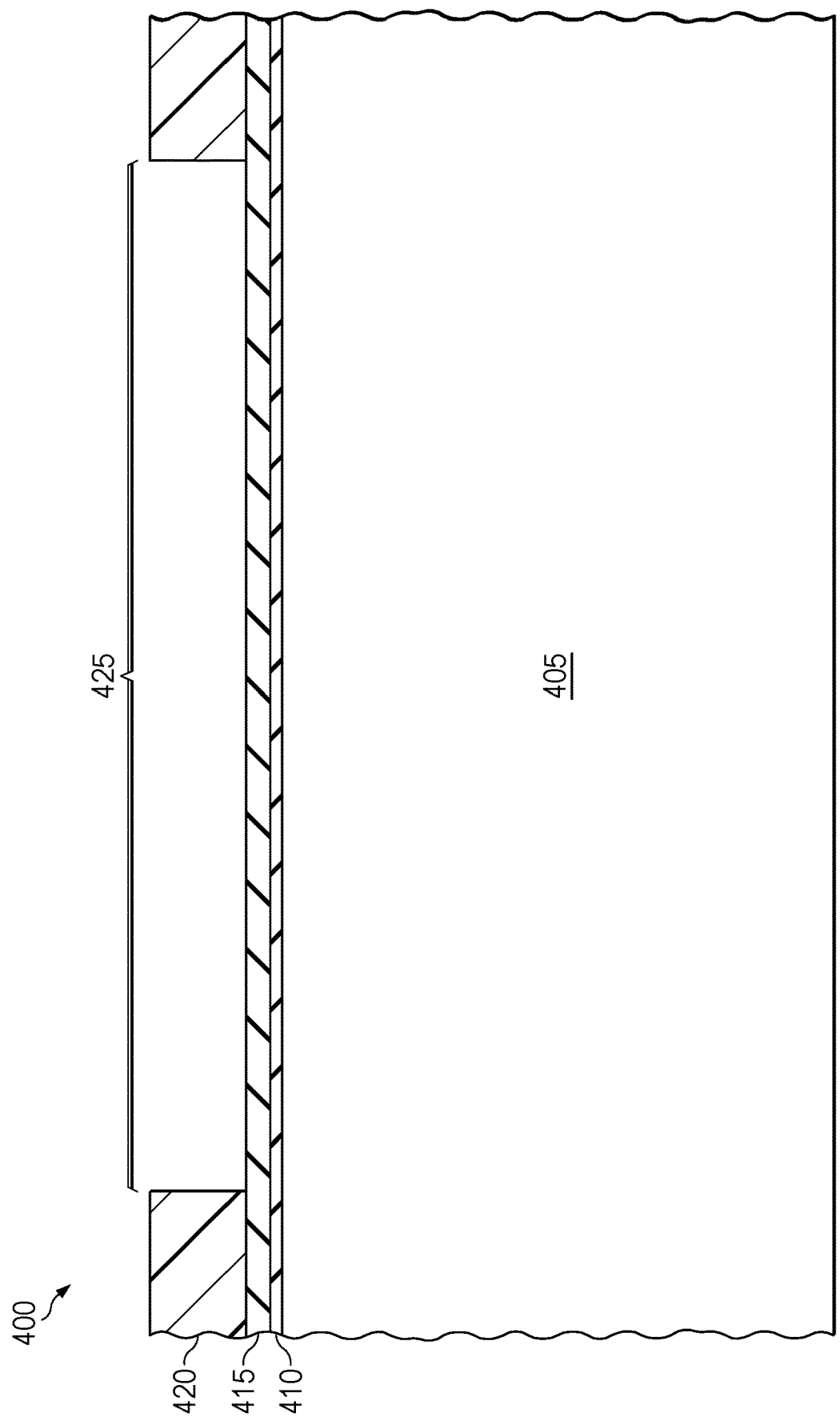

FIG. 4B illustrates the intermediate device of FIG. 4A following a known photoresist deposition, development, and strip process that results in a patterned photoresist 420. The patterned photo resist 420 that exposes a trench region 425 of the intermediate device that is to be subsequently etched.

Figure 4C:
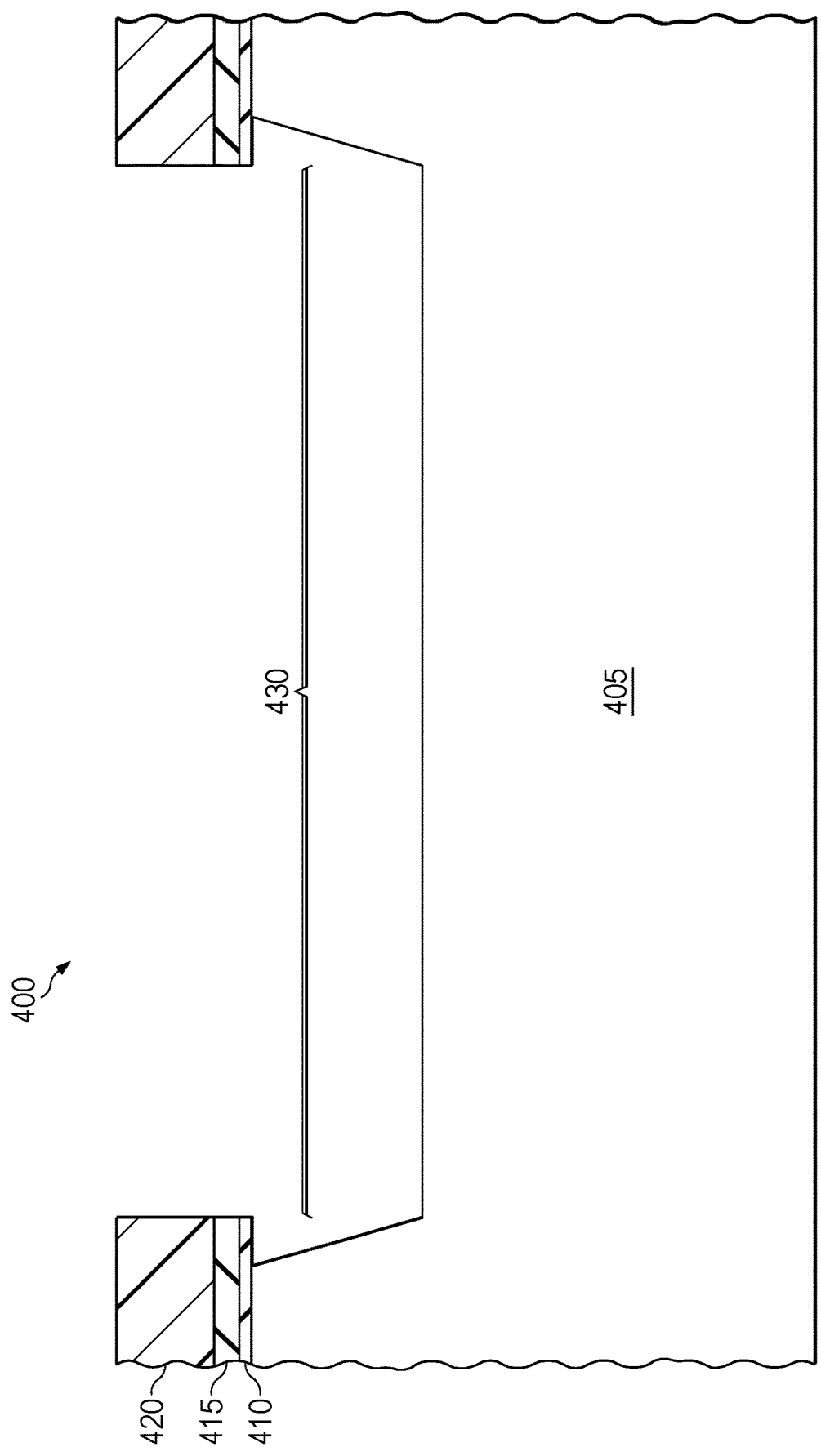

FIG. 4C illustrates the intermediate device of FIG. 4B following a known hard mask etch process, which may be either a wet or dry etch, that forms a shallow trench 430. The etch depth may vary, but in certain embodiments, the etch depth may be 3 to 6 microns. As seen, the etch undercuts a portion of the oxide layer 410 and the silicon nitride layer 415. The patterned photoresist 420, though shown, may be removed before the etch is conducted. After the etch, the silicon nitride layer 415 and oxide layer 410 are removed using known strip and cleaning processes, resulting in the intermediate device of FIG. 4D.

Figure 4D:
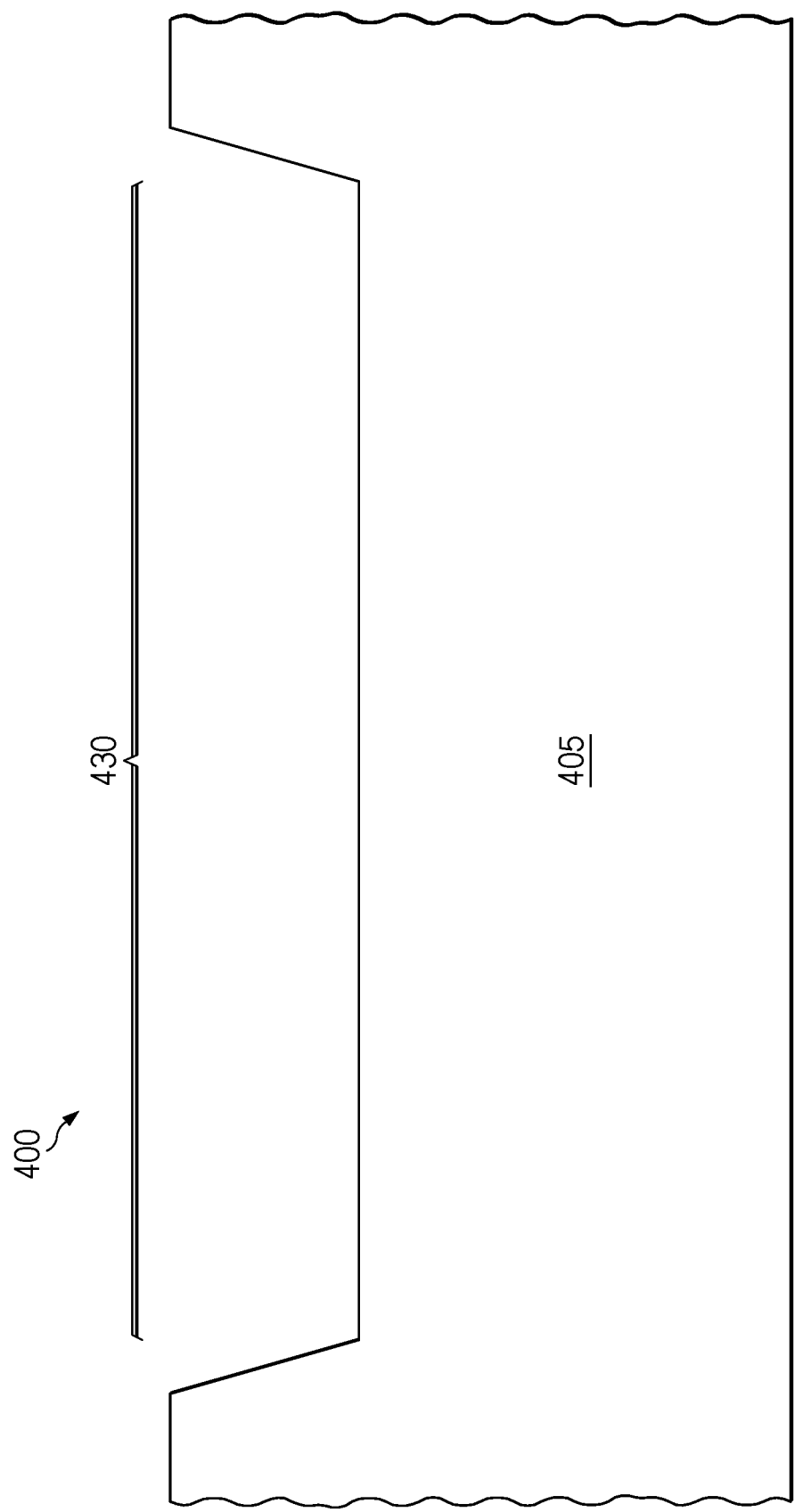
Figure 4F:
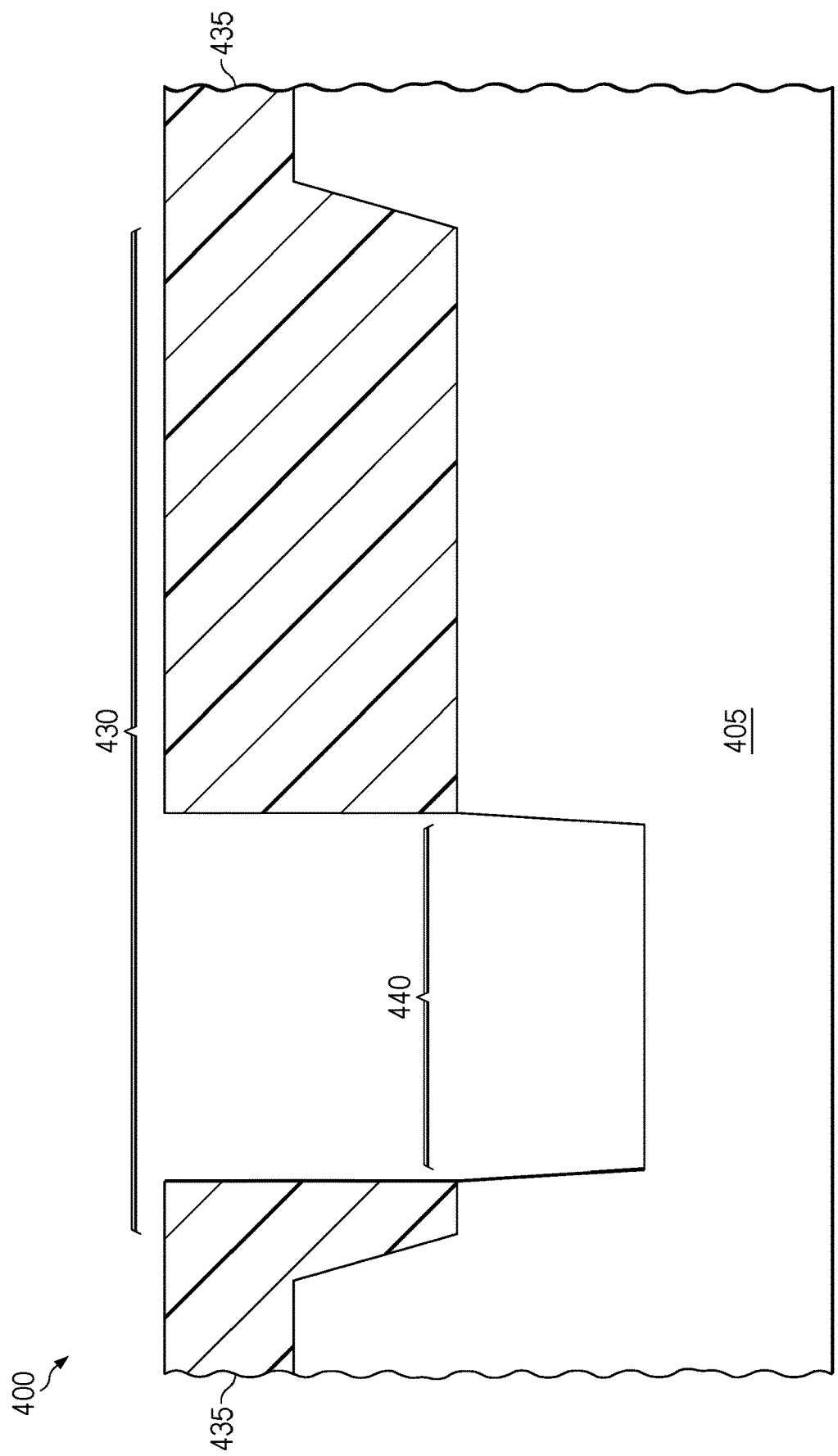

FIG. 4E illustrates the intermediate device of FIG. 4D following the deposition and patterning of a photoresist layer 435 within the shallow trench 430 that will be used to form a deeper trench. In one embodiment, a deep reactive ion etch process, such as a BOSCH etch process, may be used to etch a deep trench 440 to a depth of about 200 microns, resulting in the intermediate structure shown in FIG. 4F. Following the etch, a known strip resist ash process is conducted, flowed by a clean process, resulting in the intermediate structure shown in FIG. 4G that includes the shallow trench 430 and deep trench 440.

Figure 4G:
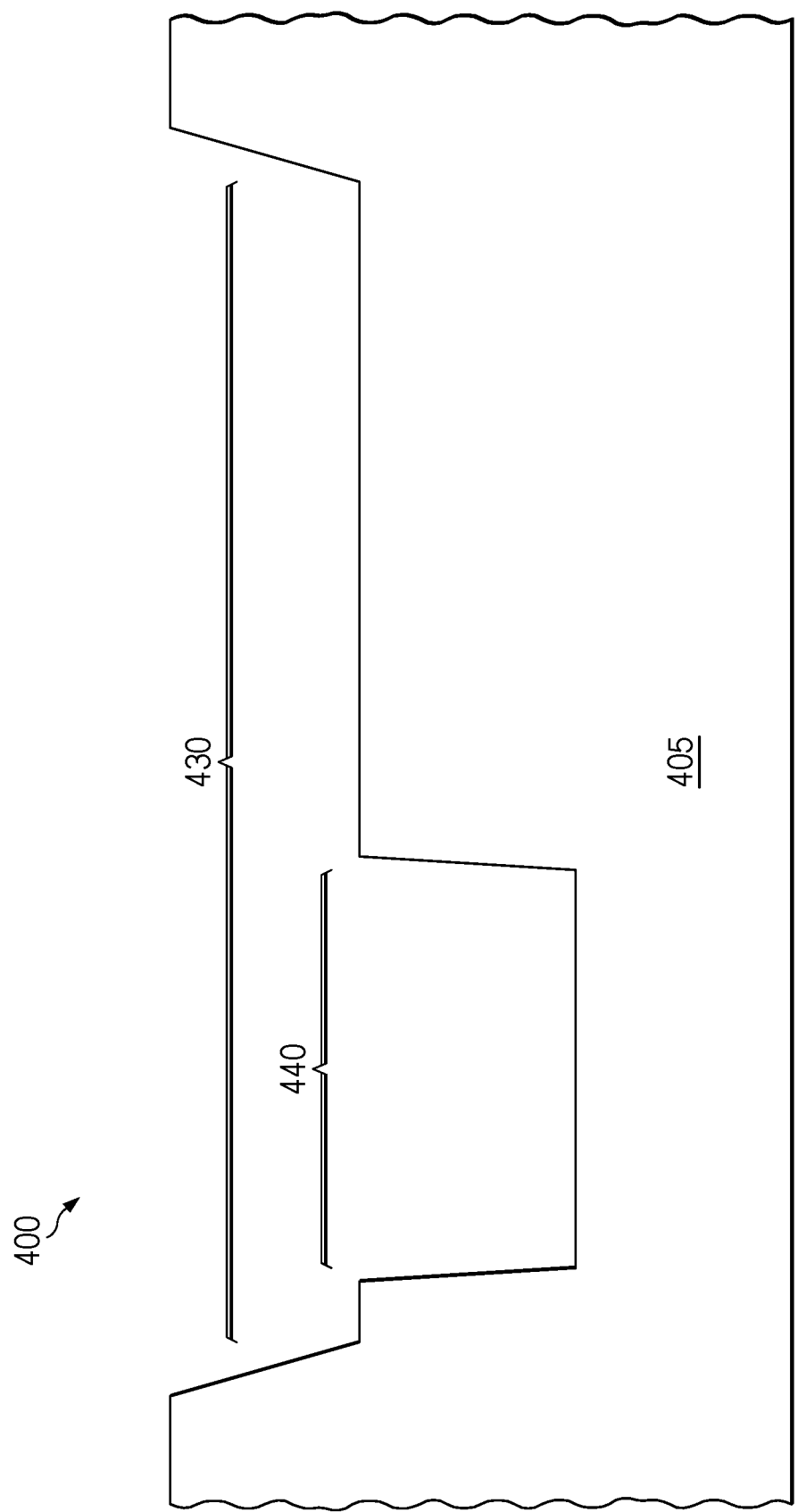
Figure 4H:
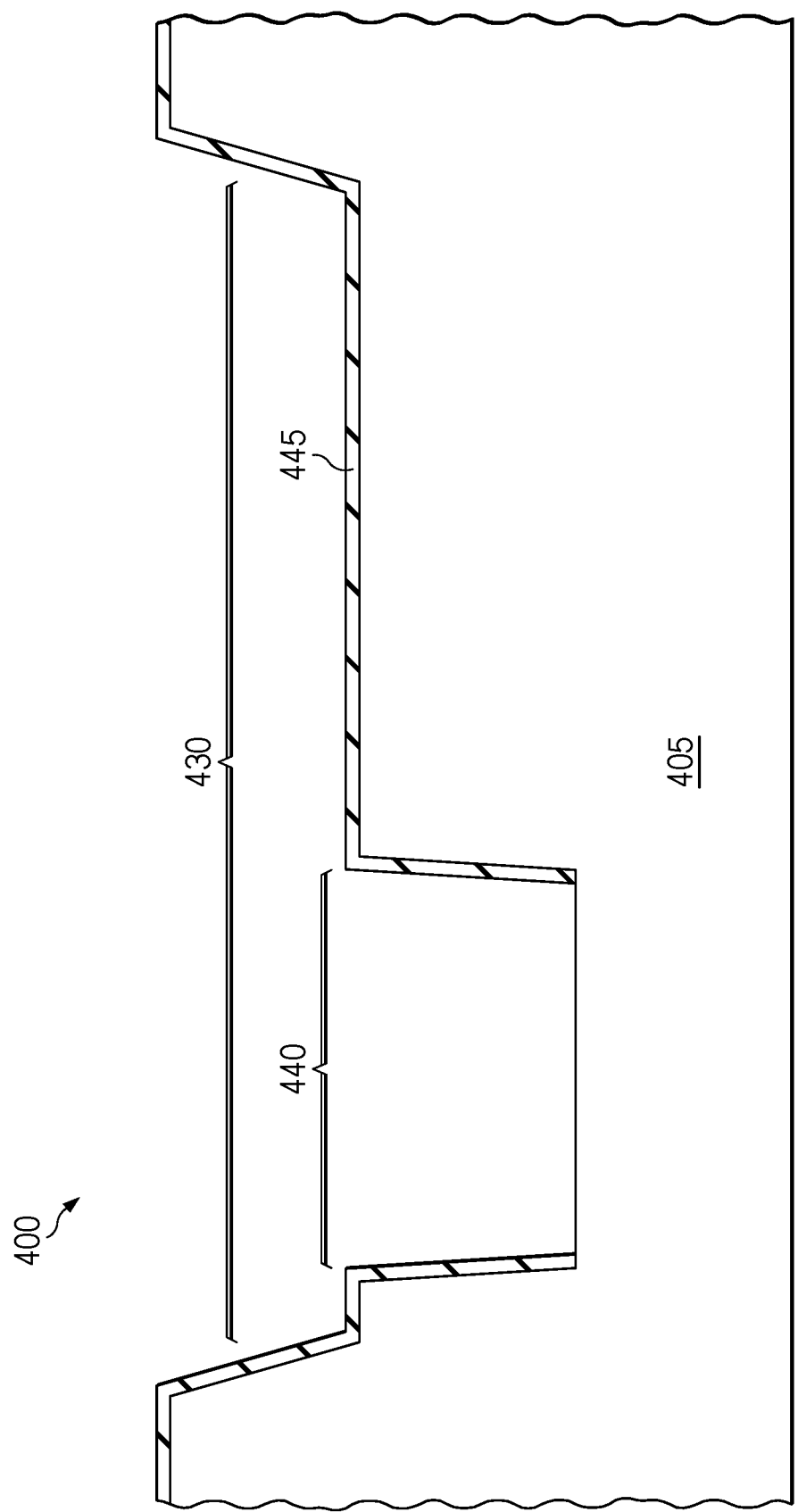

FIG. 4H illustrates the intermediate device of FIG. 4G following the removal of the photoresist and the formation of an oxide layer 445, which, in one embodiment, may be grown to a thickness ranging from about 75 nm to about 100 nm, though other thickness may be used to optimize device performance. As mentioned above, in those embodiments where a driving electrode is present, an electrode may be deposited in the bottom of the trench, or an implant may be performed to form a highly conductive region in the exposed silicon in the bottom of the deep trench 440.

Following the cleaning of the intermediate structure shown in FIG. 4H, the silicon wafer 405 with the shallow trench 430 and deep trench 440 formed therein is flipped and bonded to the photonic substrate, resulting in the general structure shown in FIG. 2.

Figure 5A:
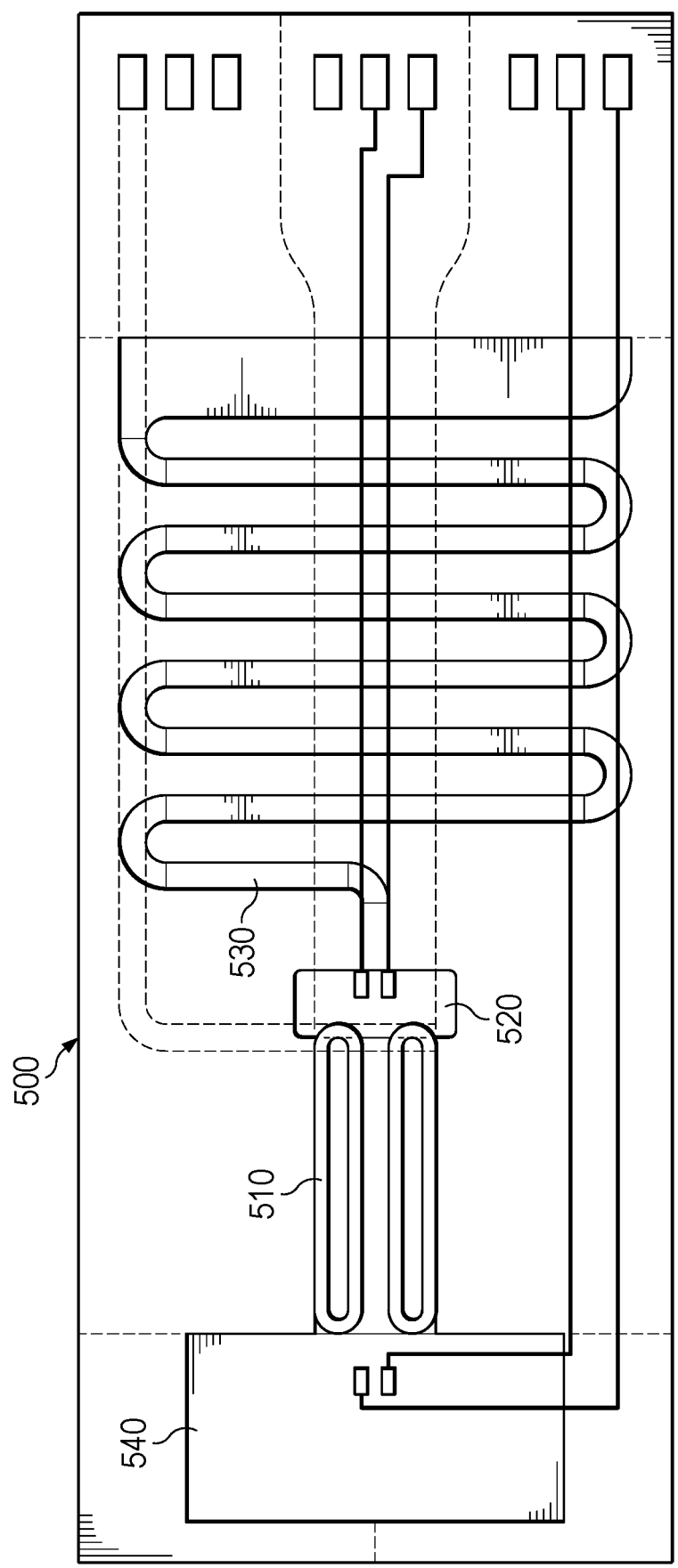
FIGS. 5A-5B illustrate layout views of different embodiments of microfluidic pumps connected to microfluidic channels of the test structure.
Figure 5B:
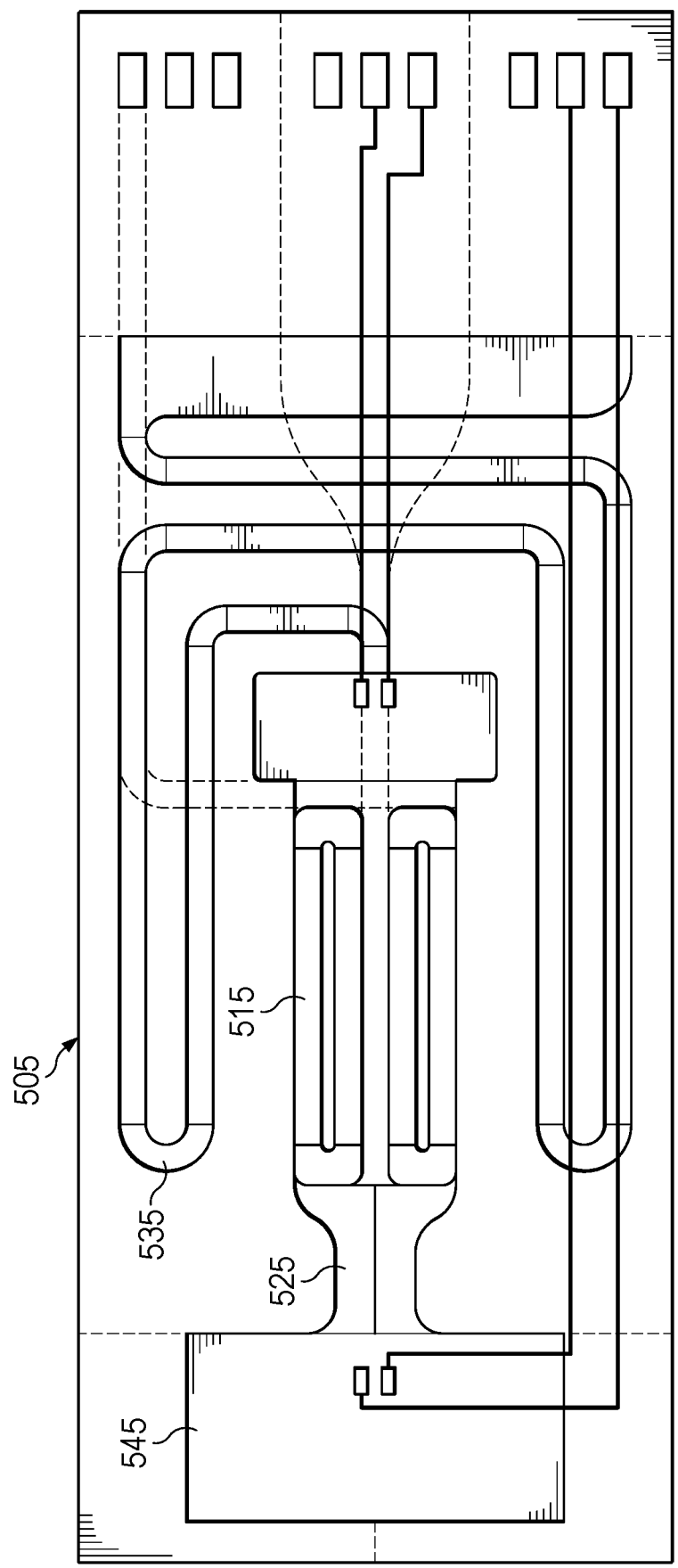

In one embodiment, the microfluidic channel 230 may be fluidly coupled to a microfluidic pump 500, 505, which are just two illustrative embodiments. FIGS. 5A-5B show examples of a couple of embodiments, but the microfluidic pumps 500, 505 may be designed as any number of serpentine configurations, as generally illustrated by FIGS. 5A and 5B. As seen in FIGS. 5A-5B, the enhanced/modified waveguides 510, 515 and their associated microfluidic channels 520, 525 and microfluidic pumps 530, 535 may have several geometrical configurations that can be used to optimize the length of the respective waveguides 510, 515 for a particular application. However, depending on design parameters, in some embodiments, the microfluidic channels 520 525 may not have an associated microfluidic pump. For example, if design parameters so require, the length of the enhanced/modified waveguide 510, 515 and microfluidic channels 520, 525, may be sufficiently short so as not to require a microfluidic pump. In other embodiments where design parameters require, the enhanced/modified waveguide 510, 515 and associated microfluidic channels 520, 525, respectively, be may longer or more complex as seen in FIGS. 5A-5B. In such embodiments, where the microfluidic pump is present, the analyte is introduced into the microfluidic channel 520, 525, through the fluid input port 540, 545. The microfluidic pumps 530, 535, when present, can operate on a capillary principle to help draw the fluid through the microfluidic channel and over the waveguide so that maximum data can be obtained from the test sample. However, in other embodiments, the microfluidic pumps 530, 535 may be mechanically driven to pump the test fluid through the microfluidic channel. For example, the microfluidic pump may comprise a piezoelectric material that can be used to move the test fluid though the microfluidic channel. The length and geometric configuration of the microfluidic channels 530, 535 may vary and will be depend on design parameters and system requirements. In the illustrated embodiments, the microfluidic channels 520, 525, and microfluidic pumps 530, 535 have a general serpentine configuration, but as just mentioned, other geometric configurations are within the scope of this disclosure. Known lithographic processes and materials may be used to fabricate the microfluidics channel.

Figure 6A:
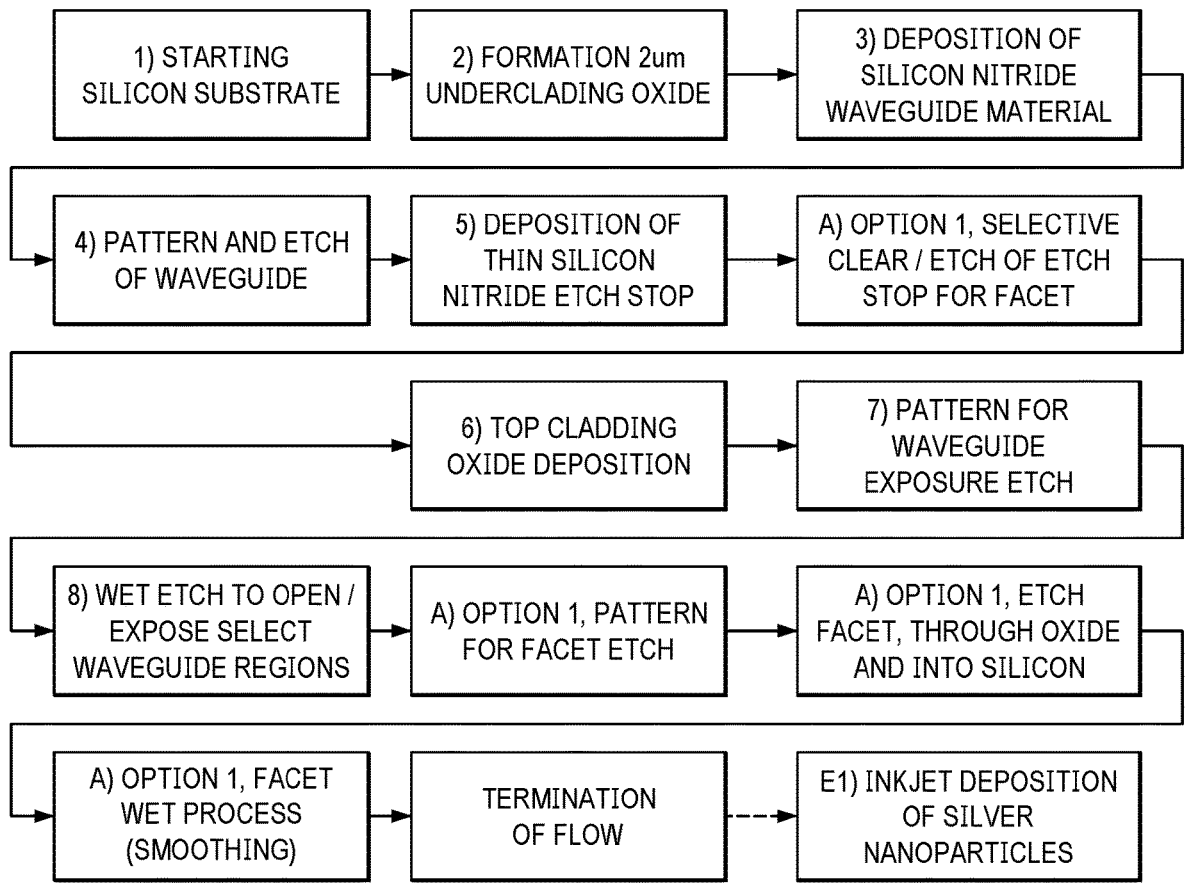
FIGS. 6A-6B illustrate flow charts of process embodiments used to fabricate the waveguide of the test structure.
Figure 6B:
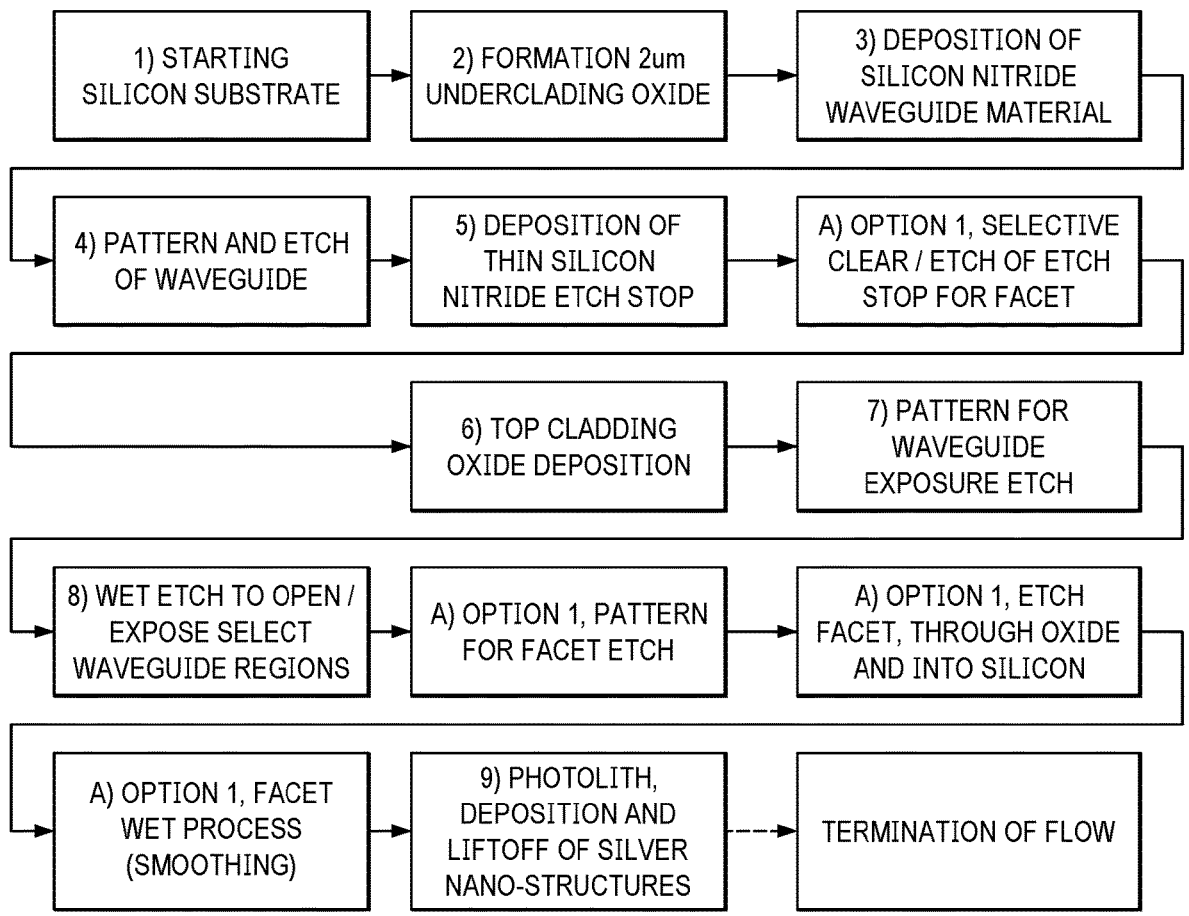

FIGS. 6A-6B illustrate examples of different process flows that can be used to fabricate different embodiments of the test structure, as described above. The flow charts are general in nature and other known intermediate steps that are not specifically stated may also be conducted, and are therefore, also within the scope of these embodiments. In the embodiment of FIG. 6A, step 1 starts with providing a silicon substrate, either from a third-party supplier or from a source internal to the manufacturer. In step 2, the under cladding oxide is formed to a thickness of about 2 microns. In step 3, silicon nitride waveguide material is deposited. In one embodiment, the minimum waveguide width is about 300 nm. In step 4, the silicon nitride waveguide material is patterned and etched using a photoresist and lithography process to form a plurality of waveguides. In step 5, which in certain embodiments may be optional, a silicon nitride etch stop layer is deposited on the patterned waveguides. In an optional step A), a selective clear/etch of an optical facet may be conducted form the optical facets at the end of the waveguides. In step 6, a top cladding of oxide is deposited over the etched waveguides. In one embodiment, the top cladding oxide has a thickness of about 2 microns. In step 7, the top cladding oxide is patterned with a photoresist to expose sensor waveguides. In step 8, an oxide etch is conducted to expose selected waveguide regions, while other waveguide lengths remain covered with the cladding oxide. An optional pattern for facet etch may be conducted through the underlying oxide and into the silicon substrate, after which an optional facet wet process can be conducted for further smoothing. In step E1, inkjet deposition of silver nanoparticles, for example, is used to deposit them onto the exposed waveguides. In one embodiment, the inkjet deposition can occur in conjunction with bonding adhesive material, as an external process.

In an alternative embodiment process flow of FIG. 6B, step 1 starts with providing a silicon substrate, either from a third-party supplier or a source internal to the manufacturer. In step 2, the under cladding oxide is formed to a thickness of about 2 microns. In step 3, silicon nitride waveguide material is deposited. In one embodiment, the minimum waveguide width is about 300 nm. In step 4, the waveguide is patterned and etched using a photoresist and lithography process to form a plurality of waveguides. In step 5, which may be an optional step, in some embodiments, a silicon nitride etch stop layer is deposited on the patterned waveguides. In an optional step A), a selective clear/etch of an optical facet may be conducted at the terminational ends of the optical waveguides. In step 6, a top cladding of oxide is deposited over the patterned nitride waveguides. In one embodiment, the top cladding oxide has a thickness of about 2 microns. In step 7, the top cladding oxide is patterned with a photoresist over sensor waveguides. In step 8, an oxide etch is conducted to expose selected waveguide regions, while other waveguide lengths remain covered with the cladding oxide. An optional pattern for facet etch may be conducted through the underlying oxide and into the silicon substrate, after which an optional facet wet process can be conducted for further smoothing. In step 9, a lithographic process is conducted by the deposition and liftoff of silver nanostructures. Though silver is mentioned, other metals, such as gold, platinum or palladium may be used. Alternatively, in place of the lithographic process, a known e-beam lithography may be conducted to deposit and liftoff of the silver nanostructures.

Figure 7:
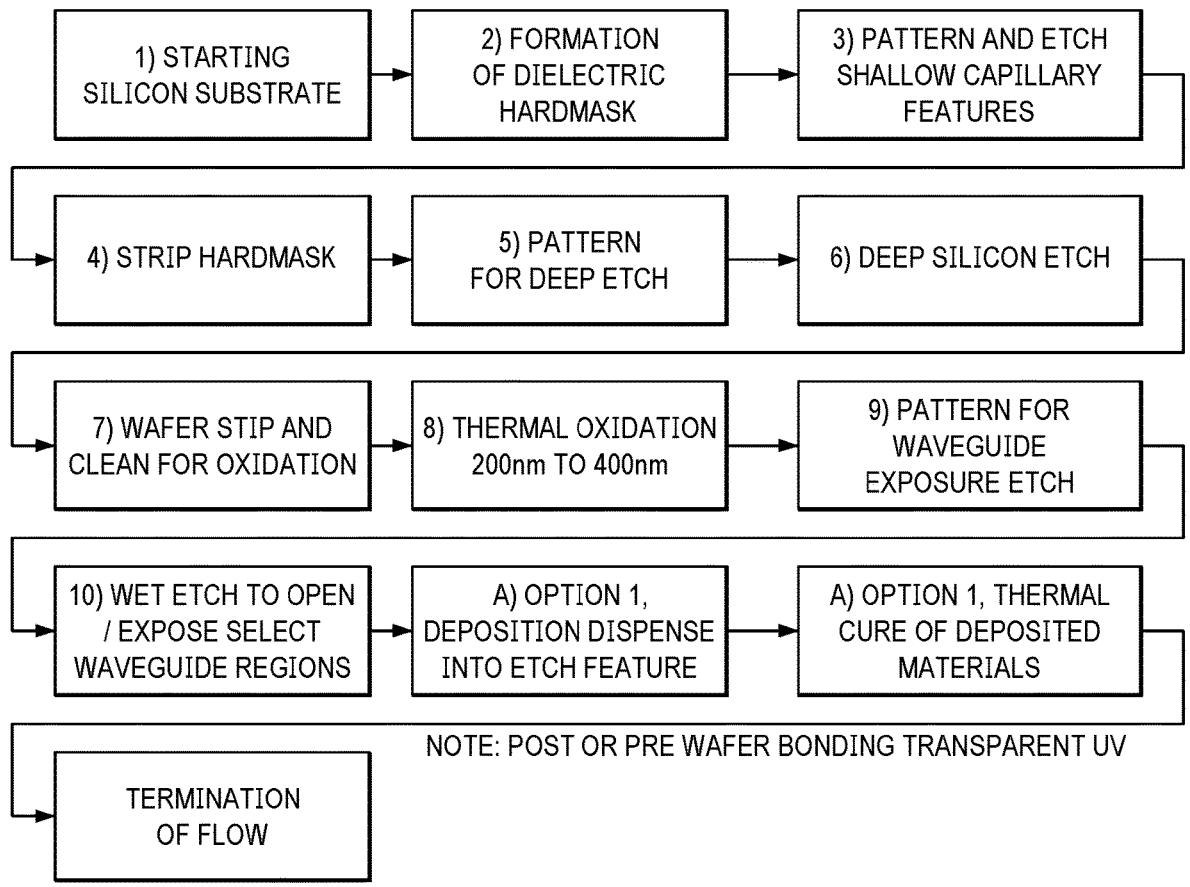
FIG. 7 illustrate a flow chart of a process embodiment used to fabricate the microfluidic channel.

FIG. 7, illustrates an embodiment of a process flow for forming the microfluidic channel, as described above. Step 1 starts with providing a silicon substrate, either from a third-party supplier or a source internal to the manufacturer. In step 2, a dielectric hard mask is formed. In one embodiment, the hard mask may include a nitride layer. In step 3, a pattern and etch is conducted to form the shallow trench, whose depth may range from about 3 microns to about 6 microns. In step 4, the hard mask is stripped. In step 5, photoresist is deposited and patterned for a deep etch used to form the deep portion of the trench. In step 6, the deep silicon etch is conducted. The depth of the deep trench may be about 200 microns. In step 7, the wafer is stripped and cleaned for oxidation. In step 8, a thermal oxidation process is conducted to form an oxide layer having a thickness that ranges from about 200 micros to about 400 microns. In step 9, the substrate is patterned for waveguide exposure and etch, and in step 10, a wet etch is conducted to open/expose select waveguide regions. In an optional step A) a material may be selectively deposited into vent/fee etched ports to limit incursion of grind byproducts into the microfluidic channel, after which the material is subjected to a thermal cure of the deposited materials.

Figure 8:
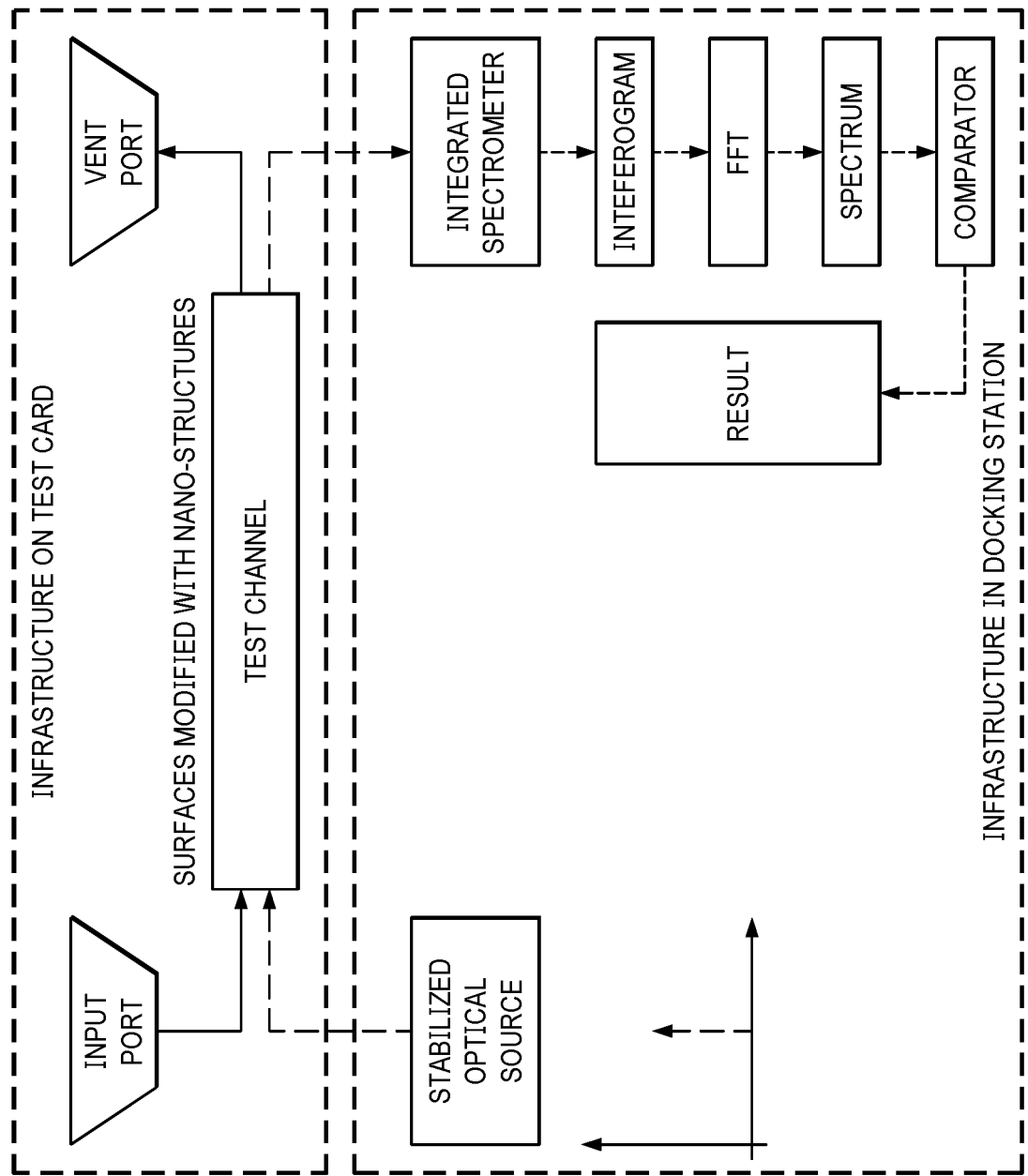
FIG. 8. illustrates an embodiment of a block diagram of an embodiment of the test card and structure, and the docking station.

FIG. 8 illustrates a general layout of one embodiment of the docking station and the test card. As seen in this schematic view, the test card includes the optical waveguide testing structure that includes the microfluidic channel and waveguide, as modified by the nanostructures or nanoparticles, as discussed above. The test card, which is a passive device, includes an input port for receiving the test sample therein and a vent port to allow for easy fluid flow into the microfluidic channel. Since the test card is passive, it may be discarded after use. When inserted into the housing of the docking station, the waveguide of the test card optically aligns with the optical circuit of the docking station. The docking station comprises the active components of the testing apparatus, which allows it to be used after sterilization. For example, it comprises an optical source, as discussed below, and integrated spectrometer that produces an interferogram, which then undergoes a Fourier transformation that produces a spectrum. The spectrum is then compared to a known spectrum signature by a comparator, after which a result is outputted by the docking station.

In operation, the test fluid is placed into the microfluidic channel through an input port. A stabilized optical source of the docking station is then guided within the waveguide of the test card down the channel. Since, the region where the channel and optical waveguide is relatively long, the evanescently guided region around or between the waveguides will interact with a larger number of target analytes and increased data can be obtained through the summation of the interactions, thereby enhancing the accuracy of the test. At the end of the sensor region, the optical signal is then input into an integrated spectrometer that measures properties of light over the specific portion of the electromagnetic spectrum associated with the subject molecule or pathogen.

These spectrometers may take the form of a wide range of integrated structures, from resonator coupled detectors to scanned structures such as the interferometers discussed below. The phase induced propagation variation in one arm, versus the fixed length of a reference arm, introduces an interference pattern interferogram, which is then transmitted to an external processor. This is then, by means of a Fast Fourier Transform (FFT), converted to the spectrum from which a unique fingerprint, consisting of unique peak positions, widths, and shapes. The spectrum is further processed by a comparator to obtain the final data set that can be transmitted to a detectable format, such as a visual signal or alphanumeric readout.

Figure 9:
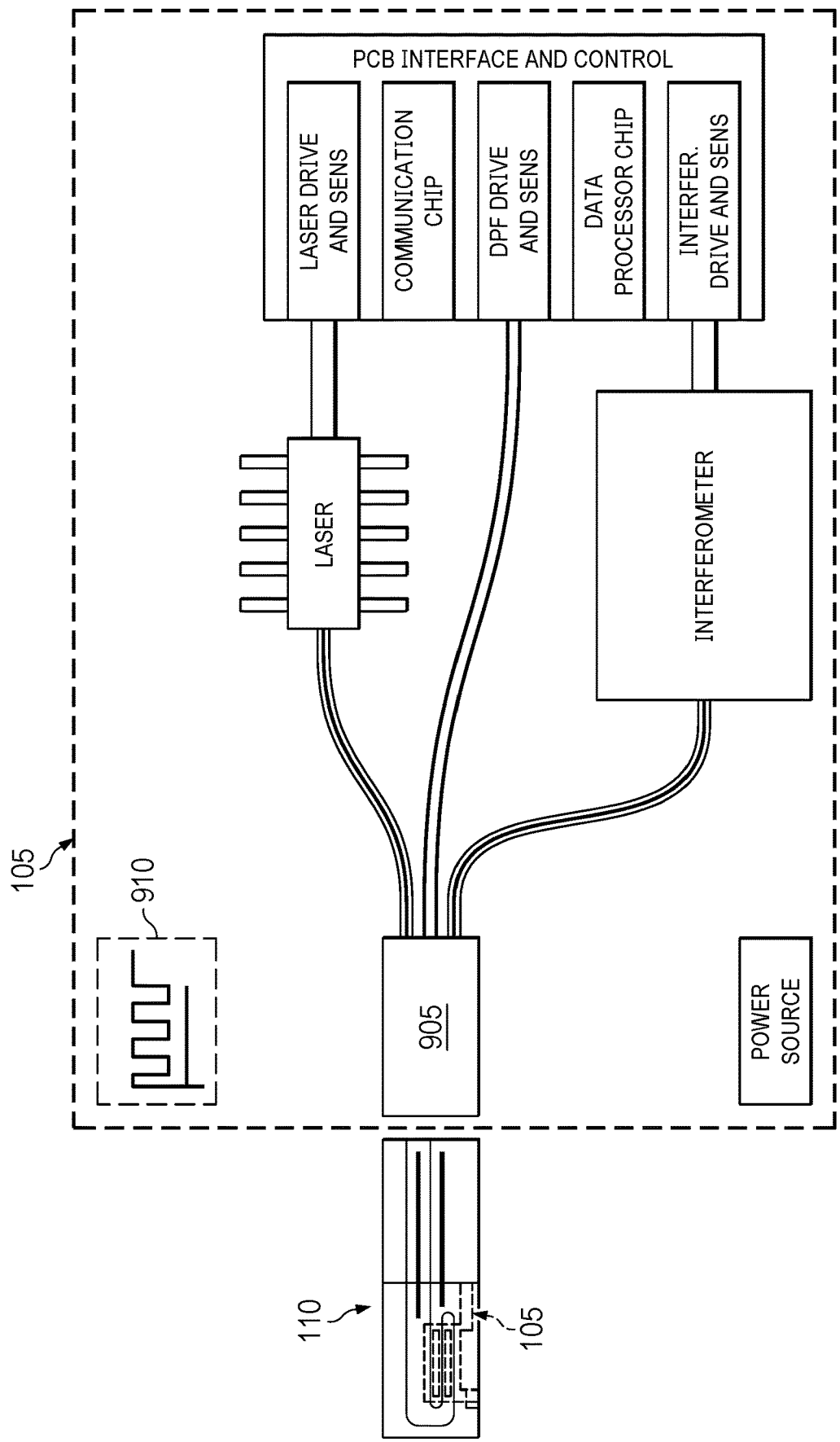
FIG. 9 illustrates an embodiment of a block diagram showing different components within an embodiment of the docking station.

FIG. 9 shows a schematic block layout of the interior components of the docking station 105 and test card 110 that includes the test structure 115. In the illustrated embodiment, the docking station 105 comprises a housing, indicated generally by the dashed line. Contained within the docking station 105 are several components. In the illustrated embodiment, the docking station comprises, a test card interface 905, such as those discussed above, a light source, such as a laser, a laser driver and sensor, a communications chip that is connected to an antenna 910 for wireless transmission of data, a DPF Driver and Sensor, a Data Processor, an interferometer Driver and Sensor that are coupled to an Interferometer, such as a Raman Spectrometer, and a power source, all of which are operatively connected to a PCB interface and controller. As used herein and in the claims, operatively coupled means that the components are coupled, either optically, electrically, or wirelessly, or a combination thereof to provide an operative unit for obtaining and analyzing data and providing and/or transmitting test results. As previously, mentioned the waveguide of the test card optically aligns with the optical components, the laser and interferometer, of the docking station, while also making appropriate connection with the electrical circuit of the docking station.

In the embodiment of FIG. 9, photonic integration is combined with microfluidics and additive manufacturing to quickly implement a compact Raman Spectroscopy based system to provide detection and identification of pathogens infecting the human population.

The photonic integrated circuit Fourier-transform (FT) spectrometer generates its output spectrum by modulating the radiation in the time domain through interference, which then undergoes a Fourier transformation. The interference between the signal propagating along the phase modulated arm, and the non-phase modulated arm are reflected to the coupler where the variation in phase causes an amplitude change. When this recorded, time-based amplitude information is recorded against the driving voltage or resulting effective path length variation in the modulated arm, it is called an interferogram, I(xeff). This Interferogram represents a modulated radiation signal as a function of the change in effective path length between the two arms of the interferometer. In the interferometric photonic circuit, the analog signal is recorded at the photodetector, which encodes the wavelength or the wave number information of the encoded Raman spectrum. A Fourier-transform routine is then performed on the interferogram to recover the Raman spectrum. An advantage of this system is the photonic integrated circuit, stabilized optical source. In one embodiment, a resonant cavity is used to define the initial gain distribution which is stabilized relative to the external cavity and composed of a Bragg mirror and phase tuner. This approach allows the control over the phase and frequency content of the signal being reinjected for injection locking of the resonant gain stage.

As mentioned above, one embodiment of this disclosure uses Raman spectroscopy, though other types of spectrometers may also be used. Raman spectroscopy is a technique in which incident laser light is inelastically scattered from a sample and shifted in frequency by the energy of its characteristic molecular vibrations. The Raman spectrum provides high informational content on the chemical structure of the probed substances, which makes this method an ideal tool for the identification of Viruses and Bacteria, illicit drugs, pharmaceutical and drug manufacturing monitoring/validation or cancer cell detection and identification. However, unlike known process that focus the Raman beam on a single point on a surface containing a targeted subject matter, the embodiments of this disclosure provide for a structure that collects data along at least a portion of the length of the waveguide or waveguides, greatly enhancing the quantity and accuracy of the data.

In practice, the test fluid is injected into the microfluidic channel providing confinement of the molecules under test. This confinement ensures the greatest overlap of the molecules with the probe beam. Further, it provides intimate and strong interaction of the molecules with nanostructures along the walls of the waveguide located in the microfluidic channel, which provides enhanced Raman Signal strength over known devices and processes.

The application of Surface-enhanced Raman spectroscopy (SERS), to improve signal strength is a modification of Raman spectroscopy. It has been demonstrated as a very capable approach to identify biomolecules, such as a bacterium or viruses. It is based on the enhancement of the Raman scattering signal of certain molecules when they are adsorbed or placed in the proximity of appropriate metallic nanostructures, usually noble metals such as silver, gold, or copper. It has been shown that the SERS approach can yield enhancement factors as large as $10^{14}$-$10^{15}$, leading to Raman scattering cross sections larger than those of fluorescent organic dyes or other reagents used in modern test sets or detection panels.

The embodiments of this discloser detect the Raman spectrum from the SERS interactions using a detector coupled with an interferometer, embodiments of which are generally shown in FIG. 9. This unique approach generates an interferogram that contains the frequency dependent information modulated in a time domain as a function of the phase propagation length variation in one arm of the spectrometer. The system will then perform a Fourier-transform to extract the detailed Raman spectrum used to detect and identify viruses present in the sample.

Figure 10:
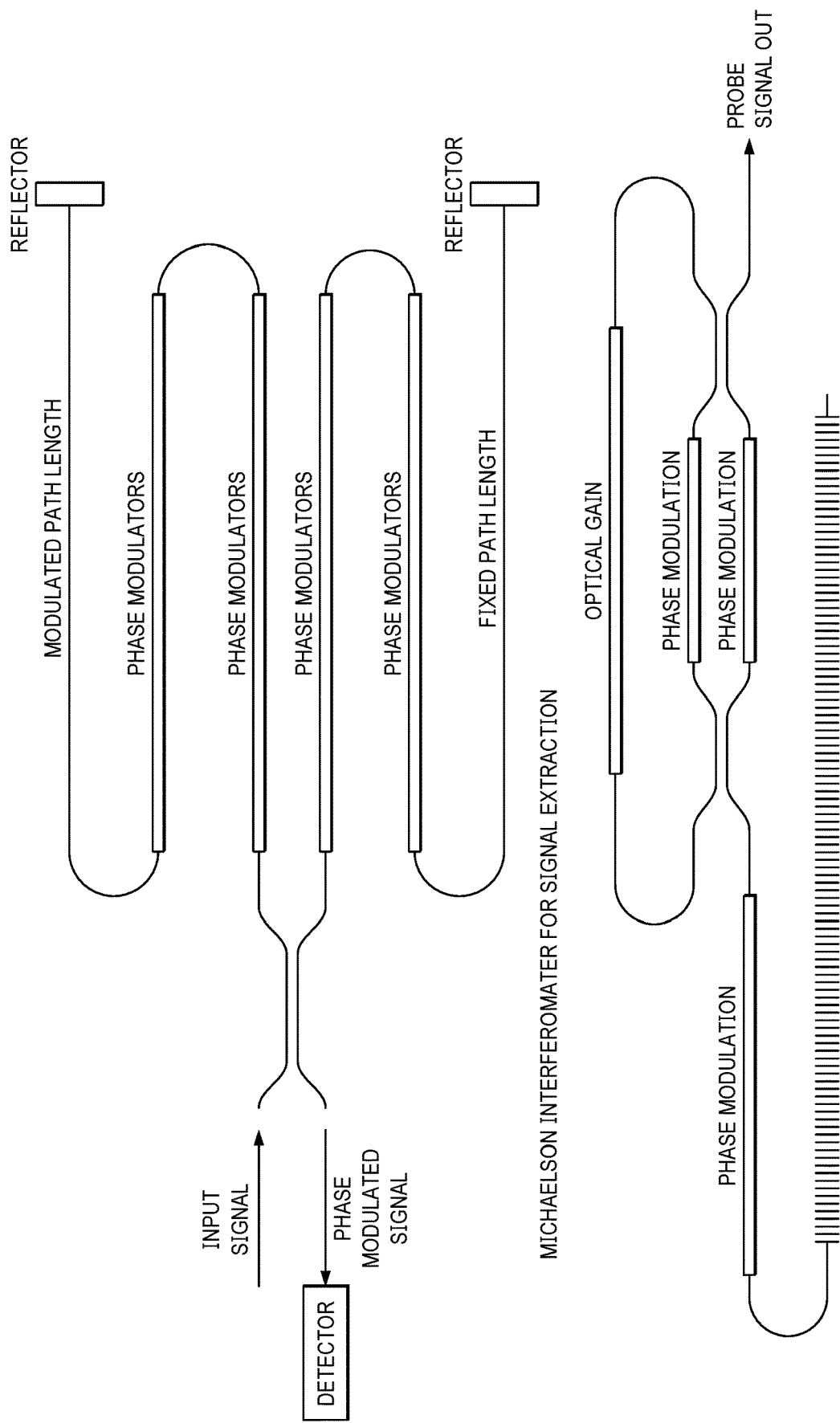
FIG. 10 illustrates layouts of an embodiment of an interferometer and a stabilized optical source.

FIG. 10 schematically illustrates an embodiment of an interferometer, such as a Michaelson Interferometer, and a stabilized optical source that can be integrated into the docking station 105, both shown as integrated photonic components. While the approach can employ fiber coupled off the shelf laser diodes operating at ~660 nm, the compact spectrometer may include the implementation of one of two configurations to provide the required spectral accuracy and wavelength span to ensure the desired level of repeatability and integration within a compact unit. The photonic integrated circuit stabilized optical source, in one embodiment, is a resonant cavity that is used to define the initial gain distribution that is stabilized relative to the external cavity and composed of a Bragg mirror and phase tuner. This approach allows the control over the phase and frequency content of the signal being reinjected for injection locking of the resonant gain stage, as seen in FIG. 10. Known lithographic process can be used to form and integrate these photonic components into the embodiment of the docking station 105, as generally illustrated in FIG. 9.

The analysis of the above-discussed embodiments is based on Raman spectroscopy from the SERS interactions using a detector coupled with an interferometer. This approach generates an interferogram which contains the frequency dependent information modulated in a time domain as a function of the phase propagation length variation in one arm of the spectrometer. A Fourier-transform to extract the detailed Raman spectrum is used to detect and identify viruses present in the sample.

Photonic integrated circuit Fourier-transform (FT) spectrometer generates its output spectrum by modulating the radiation in the time domain through interference, which then undergoes a Fourier transformation. The detection and identification of pathogens is insured by the ability to integrate 6 elements into a relatively small area, such as the illustrated dock station by leveraging semiconductor manufacturing and packaging techniques. These include: 1) the stabilized narrow band optical source to provide a controllable Raman Probe; 2) The evanescently coupled low index contrast waveguides providing controlled overlap of the modal energy traveling external to the waveguide and the metallic nanostructures which provide the photonic enhancement of the Raman Scattering; 3) Formation of nano structures between and on the waveguides providing a controlled surface region for characterization of a pathogen; 4) The integration of electrodes which allow controlled enrichment of the target pathogen at the metallic nanostructure surface; 5) The Integration of microfluidic structures to confine the sample volume relative to the waveguides and enrichment structures; 6) The ability to integrate a small Fourier transform spectrometer.

To ensure that rapid test products can be made available as quickly as possible, the embodiments disclosed herein disclose a path to an early passive test structure that allows the fielding of a simpler version of the test to be delivered in the shortest time possible.

The unique benefits that the various embodiments of the test strip detection and identification system include: the ability to confine solutions containing viral materials to a micro channel, providing improved interaction cross section between the probe beam and target materials. This will provide us with a system having multiple orders of magnitude improvement in sensitivity over any other approach; 14 to 15 orders of magnitude increase in signal sensitivity resulting from application of metallic nano structures along the walls of the micro channels providing forced interaction with multiple surfaces and increasing the overall interaction length and accumulated signal strength; low cost generation, coupling, transmission, processing and detection of the Raman spectrums, application of micro channel integration technologies to support the formation of the localized metallic nanostructures within the channels and their integration with the photonic integrated circuits and the supporting elements to control injection of the probe beam into the micro channel, guide the probe in a controlled manner through the micro channel, and re-couple the probe beam back into the photonic circuit for processing and spectrum extraction; packaging of the sensor into a useable vehicle to allow isolated, real-time single point testing without putting additional persons at risk.

Embodiment disclosed herein comprise:

One embodiment is directed to a test apparatus that comprises a test card having a coupling end, and a test structure comprising a waveguide having an uncladded sensor portion and an outer surface and side surfaces formed on a silicon substrate located on the test card, wherein the silicon substrate comprises a semiconductor material. Nanoparticles are located on or adjacent the uncladded sensor portion of the waveguide, wherein a concentration of the nanoparticles is higher on or adjacent the side surface of the waveguide than on the outer surface. The test structure includes a fluid input port located over the waveguide such that an analyte deposited into the fluid input port comes into contact with the waveguide. The test structure has an optical input end that includes optical fibers located within v-grooves on the silicon substrate that are optically coupled to the waveguide and extend to the coupling end of the test card.

Another embodiment provides a test apparatus that comprises a test card that has one or more interconnected metal levels, and a coupling end, and a test structure, comprising a waveguide having an uncladded sensor portion and an outer surface and side surfaces formed on a silicon substrate located on the test card, wherein the silicon substrate comprises a semiconductor material. Nanoparticles are located on or adjacent the uncladded sensor portion of the waveguide, wherein a concentration of the nanoparticles is higher on or adjacent the side surface of the waveguide than on the outer surface. The test structure includes a fluid input port located over the waveguide such that an analyte deposited into the fluid input port comes into contact with the waveguide. The test structure has an optical output end that includes optical fibers located within v-grooves on the silicon substrate that are optically couple to the waveguide and extend to the coupling end of the test card. This embodiment also includes a docking station for receiving the test card therein. The docking station has a housing having a test card interface that is configured to receive the coupling end of test card therein. An interferometer, and a laser is located within the housing and is optically aligned with the test structure to receive a transmission therefrom. An interferometer is also located within the housing and optically coupled to the test structure to receive an optical transmission therefrom. A data processor and control board are located within the housing. The control board is configured to control an operation of the laser, interferometer, and data processor that is operatively coupled to these components.

Element 1: wherein the test card includes one or more interconnected metal levels within the test card and the test structure includes one or more interconnect metal levels located within the silicon substrate of the test structure that are connected to the one or more interconnected metal levels of the test card.

Element 2: wherein one or more interconnected metal levels of the test structure include a driving electrode located within the silicon substrate and adjacent the waveguide.

Element 3: wherein an output end of the waveguide has a facet surface.

Element 4: wherein the test card is printed circuit board having one or more metal levels therein and the coupling end that includes surface electrodes that are electrically connected to the one or more metal levels of the test card and the one or more metal level levels of the test structure are electrically coupled to the one or more metal levels of the printed circuit board, the coupling end further comprising ferrules that are optically connected to the optical fibers of the test structure.

Element 5: wherein the waveguide includes a nitride layer located on the side surfaces and the outer surface.

Element 6: wherein the waveguide comprises silicon nitride or silicon oxynitride.

Element 7: wherein the test card comprises a v-groove fiber mount base located adjacent the coupling end of the test card, and the optical fibers of the test structure extend from the test structure to the v-groove fiber mount base and the optical fibers located within v-grooves of the fiber cap coupling end of the test card a V-groove fiber mount base, a ferrule cap, and optical ferrules extending therefrom.

Element 8: wherein the coupling end of the test card comprises a ferule cap, and optical ferrules extending therefrom, wherein the optical ferrules are optically connected to the optical fibers of the test structure.

Element 9: wherein the docking station further comprises a power source and communication circuitry for wireless transmission of data from the docking station.

Element 10: wherein the communication circuitry is coupled to an antenna for wireless transmission of the data.

Element 11: further comprising a laser driver and sensor, a dielectrophoretic fiber (DPF) driver and sensor, and an interferometer driver and sensor being operatively coupled to the control board.

Element 12: further comprising an optical stabilized source.

Element 13: wherein the interferometer is a Michaelson Interferometer.

Element 14: further comprising a spring biased clip configured to receive the test card therein and optically and electrically align the test card with the docking station.

Element 15: wherein the test structure includes one or more interconnected metal levels formed within the silicon substrate of the test structure that are connected to the one or more interconnected metal levels of the test card.

Element 16: wherein the one or more interconnected metal levels of the test structure include a driving electrode located within the silicon substrate of the test structure and adjacent the waveguide.

Element 17: wherein an output end of the waveguide has a facet surface.

Element 18: wherein the coupling end of the test card comprises a v-groove fiber mount base, a ferrule cap, and optical ferrules extending therefrom, wherein the optical fibers extend into the optical ferrules and are configured to provide optical connection to the docking station.

Although the present invention has been described in detail, those skilled in the art should understand that they can make various changes, substitutions, and alterations herein without departing from the spirit and scope of the invention in its broadest form.

What is claimed is:

1. A test apparatus, comprising:
    a test card having a coupling end; and
    a test structure located on the test card, comprising:
        a silicon substrate;
        a planar waveguide formed on the silicon substrate and having an uncladded sensor portion comprising an outer surface and side surfaces, wherein the silicon substrate comprises a semiconductor material;
        nanoparticles located on the outer surface and on the side surfaces of the uncladded sensor portion of the planar waveguide, wherein a concentration of the nanoparticles is higher on the side surfaces of the planar waveguide than on the outer surface;
        a fluid input port located over the planar waveguide and in fluid communication with the planar waveguide that allows an analyte deposited into the fluid input port to contact the planar waveguide; and
        an optical output end that includes optical fibers located within v-grooves on the silicon substrate that are optically coupled to the planar waveguide and extend to the coupling end of the test card.

2. The test apparatus of claim 1, wherein the test card includes interconnected metal levels located within the test card and the test structure includes interconnected metal levels located within the silicon substrate of the test structure that are connected to the interconnected metal levels of the test card.

3. The test apparatus of claim 2, wherein the interconnected metal levels of the test structure include a driving electrode located within the silicon substrate of the test structure and adjacent the waveguide.

4. The test apparatus of claim 1, wherein the optical output end of the waveguide is a facet surface.

5. The test apparatus of claim 2, wherein the test card is a printed circuit board having interconnected metal levels therein and the coupling end that includes surface electrodes that are electrically connected to the interconnected metal levels of the test card and the interconnected metal levels of the test structure are electrically coupled to the interconnected metal levels of the printed circuit board, the coupling end further comprising ferrules that are optically connected to the optical fibers of the test structure.

6. The test apparatus of claim 1, wherein the planar waveguide includes a nitride layer located on the side surfaces and the outer surface.

7. The test apparatus of claim 1, wherein the planar waveguide comprises silicon nitride or silicon oxynitride.

8. The test apparatus of claim 1, wherein the test card comprises a v-groove fiber mount base located adjacent the coupling end of the test card, and the optical fibers of the test structure extend from the test structure to the v-groove fiber mount base and the optical fibers are located in the V-shaped grooves in the fiber mount base.

9. The test apparatus of claim 8, wherein the coupling end of the test card comprises, a ferrule cap, and optical ferrules extending therefrom, wherein the optical ferrules are optically connected to the optical fibers of the test structure.

10. A test apparatus, comprising:
    a test card having one or more interconnected metal levels and a coupling end; and
    a test structure located on the test card, comprising:
        a silicon substrate;
        a planar waveguide formed on the silicon substrate and having an uncladded sensor portion comprising an outer surface and side surfaces, wherein the silicon substrate comprises a semiconductor material;
        nanoparticles located on the outer surface and on the side surfaces of the uncladded sensor portion of the planar waveguide, wherein a concentration of the nanoparticles is higher on the side surfaces of the planar waveguide than on the outer surface;
        a fluid input port located over the planar waveguide and in fluid communication with the planar waveguide that allows an analyte deposited into the fluid input port to contact the planar waveguide; and
        an optical output end that includes optical fibers located within v-grooves on the silicon substrate that are optically coupled to the planar waveguide and extend to the coupling end of the test card; and
    a docking station for receiving the coupling end of the test card therein,
    comprising:
        a housing having a test card interface that is configured to receive the coupling end of the test card therein;

a laser located within the housing and optically aligned with the test structure to receive a transmission therefrom;

an integrated interferometer and spectrometer located within the housing and optically couplable to the test structure to receive an optical transmission therefrom; and a data processor and control board located within the housing, the control board configured to control an operation of the laser, interferometer, and data processor and being operatively coupled thereto.

11. The test apparatus of claim 10, wherein the docking station further comprises a power source and communication circuitry for wireless transmission of data from the docking station.

12. The test apparatus of claim 11, wherein the communication circuitry is coupled to an antenna for wireless transmission of the data.

13. The test apparatus of claim 10, further comprising a laser driver and sensor, a dielectrophoretic filter (DPF) driver and sensor, and an interferometer driver and sensor being operatively coupled to the control board.

14. The test apparatus of claim 10, wherein the docking station further comprising a spring biased clip configured to receive the test card substrate therein and optically and electrically align the test card substrate with the docking station.

15. The test apparatus of claim 10, wherein the test structure comprises one or more interconnected metal levels formed within the silicon substrate of the test structure connected to the one or more interconnected metal levels of the test card.

16. The test apparatus of claim 15 wherein the one or more interconnected metal levels of the silicon substrate of the test structure include a driving electrode located within the first silicon substrate and adjacent the waveguide.

17. The test apparatus of claim 10, wherein the optical output end of the planar waveguide is a facet surface.

18. The test apparatus of claim 10, wherein the coupling end of the test card comprises, a ferrule cap, and optical ferrules extending therefrom, wherein the optical ferrules are optically connected to the optical fibers and wherein the optical fibers extend into the optical ferrules and are configured to provide optical connection to the docking station.

* * * * *